United States Patent
Sorenson

(10) Patent No.: US 10,978,184 B2
(45) Date of Patent: Apr. 13, 2021

(54) EVOLVING CONTEXTUAL CLINICAL DATA ENGINE FOR MEDICAL INFORMATION

(71) Applicant: Jeffrey Sorenson, Milwaukee, WI (US)

(72) Inventor: Jeffrey Sorenson, Milwaukee, WI (US)

(73) Assignee: TeraRecon, Inc., Foster City, CA (US)

( * ) Notice: Subject to any disclaimer, the term of this patent is extended or adjusted under 35 U.S.C. 154(b) by 667 days.

(21) Appl. No.: 14/530,520

(22) Filed: Oct. 31, 2014

(65) Prior Publication Data

US 2015/0127379 A1 May 7, 2015

Related U.S. Application Data

(60) Provisional application No. 61/899,699, filed on Nov. 4, 2013, provisional application No. 61/909,920, filed on Nov. 27, 2013, provisional application No. 61/911,302, filed on Dec. 3, 2013, provisional application No. 61/984,624, filed on Apr. 25, 2014.

(51) Int. Cl.
| | |
|---|---|
| *G16H 10/60* | (2018.01) |
| *G16H 50/20* | (2018.01) |
| *G16H 10/20* | (2018.01) |
| G16H 30/20 | (2018.01) |

(52) U.S. Cl.
CPC ............ *G16H 10/60* (2018.01); *G16H 10/20* (2018.01); *G16H 50/20* (2018.01); *G16H 30/20* (2018.01)

(58) Field of Classification Search
CPC ............................. G06Q 50/22; G06Q 50/24
See application file for complete search history.

(56) References Cited

U.S. PATENT DOCUMENTS

| | | | |
|---|---|---|---|
| 6,216,104 B1 * | 4/2001 | Moshfeghi | ............ G06F 19/325 |
| | | | 704/260 |
| 6,735,272 B1 | 5/2004 | Sorenson | |
| 7,430,308 B1 | 9/2008 | Kallergi | |
| 7,912,528 B2 | 3/2011 | Krishnan et al. | |

(Continued)

FOREIGN PATENT DOCUMENTS

JP        2009512010        3/2009

OTHER PUBLICATIONS

Asur, Sitaram, "An event-based framework for characterizing the evolutionary behavior of interaction graphs," Dec. 2009, ACM Transactions on Knowledge Discovery from Data, vol. 3, Issue 4. (Year: 2009).*

*Primary Examiner* — Lena Najarian
(74) *Attorney, Agent, or Firm* — Douglas L. Weller

(57) ABSTRACT

A medical information server receives a signal from a client device over a network, representing a first user interaction of a user with respect to first medical information displayed to a user. A user interaction analyzer invokes a first set of ECCD rules associated with the user based on the first user interaction to determine medical data categories that the user is likely interested in. The first set of ECCD rules was generated by an ECCD engine based on prior user interactions of the user. A data retrieval module accesses medical data servers corresponding to the medical data categories to retrieve medical data of the medical data categories. A view generator integrates the retrieved medical data to generate one or more views of second medical information and transmits the views of second medical information to a client device to be displayed on a display of the client device.

30 Claims, 18 Drawing Sheets

(56) References Cited

U.S. PATENT DOCUMENTS

| | | | |
|---|---|---|---|
| 2002/0186820 A1* | 12/2002 | Saito | G06F 19/321 378/210 |
| 2005/0021377 A1 | 1/2005 | Dobbs et al. | |
| 2006/0052945 A1* | 3/2006 | Rabinowitz | G06F 19/24 702/20 |
| 2006/0111936 A1* | 5/2006 | Mahesh | G06F 19/321 705/2 |
| 2006/0242146 A1* | 10/2006 | Piacsek | G06K 9/4609 |
| 2006/0282302 A1* | 12/2006 | Hussain | G06F 19/327 705/2 |
| 2007/0066911 A1 | 3/2007 | Klingenbeck-Regn | |
| 2007/0143736 A1* | 6/2007 | Moriarty | G06Q 10/06 717/100 |
| 2008/0025583 A1 | 1/2008 | Jabri et al. | |
| 2009/0136111 A1 | 5/2009 | Jabri et al. | |
| 2009/0282023 A1* | 11/2009 | Bennett | G06F 17/30646 |
| 2013/0208955 A1 | 8/2013 | Zhao et al. | |
| 2015/0019261 A1* | 1/2015 | Horrell | G06F 17/30554 705/3 |

\* cited by examiner

EVOLVING CONTEXTUAL CLINICAL DATA ENGINE FOR MEDICAL INFORMATION

RELATED APPLICATIONS

This application claims the benefit of U.S. Provisional Application No. 61/899,699 filed Nov. 4, 2013, Application No. 61/909,920 filed Nov. 27, 2013, Application No. 61/911,302 filed Dec. 3, 2013, and Application No. 61/984,624 filed Apr. 25, 2014, the disclosure of which is incorporated by reference herein in its entirety.

FIELD OF THE INVENTION

Embodiments of the present invention relate generally to medical information processing systems. More particularly, embodiments of the invention relate to medical information processing using an evolving contextual clinical data (ECCD) engine.

BACKGROUND

As medical software becomes more sophisticated and universal, intelligent integration of information and data from different data sources becomes more important and more challenging. For example, electronic medical records (EMRs) or electronic health records (EHRs) are becoming increasingly common as is clinical trials software, research software as well as others. But medical data resides in several data sources that do not communicate well together, including a radiology information system (RIS), a hospital information system (HIS), a picture archiving and communication system (PACS), a laboratory information system (LIS), an enterprise content management (ECM) system, EMR data, various directories as well as other data sources. These data sources may be provided in various servers operated by different organizations or entities.

In addition to the lack of communication among various data sources, medical software, such as EMR, HER, clinical trial software etc., even where they do connect with one or more of these data sources, do not present the information in an intelligent nor useful manner. A user, such as a physician, technician, patient etc., needs to access all of the information that is relevant easily and without having to actively open several different software packages, search for the patient, and then search for the information that is pertinent.

For example, if a patient is being treated for lung cancer, his physician needs to view the patient's medications, relevant procedures he/she has had, results of the procedures, results of relevant lab tests, demographic data, relevant notes, reports, dictation, etc. The physician does not need to view an x-ray of a broken toe, for example.

Currently this is not practical within any medical software packages. Some EMR software allows a user to view a static image, such as an X-ray, along with the demographic data, but the user is not able to easily view all relevant information together. Currently, the user must know where to find the relevant information and back out of screens, directories, search windows etc. to view it, or locate the information on a different system with a different login etc. Although some connectors to the various data sources exist, there does not exist an engine, or system, which has the knowledge to display relevant data at the same time, in a way that is useful to the end user.

There is a need for an intelligent system which can not only connect to varied and different data sources, but display relevant information, in context, to the end user in a way that is useful. Ideally such an intelligent system will display the relevant information from different data sources to the user, in context, within a viewer which is organized in a logical way to display the data.

BRIEF DESCRIPTION OF THE DRAWINGS

Embodiments of the invention are illustrated by way of example and not limitation in the figures of the accompanying drawings in which like references indicate similar elements.

DETAILED DESCRIPTION

Figure 1:
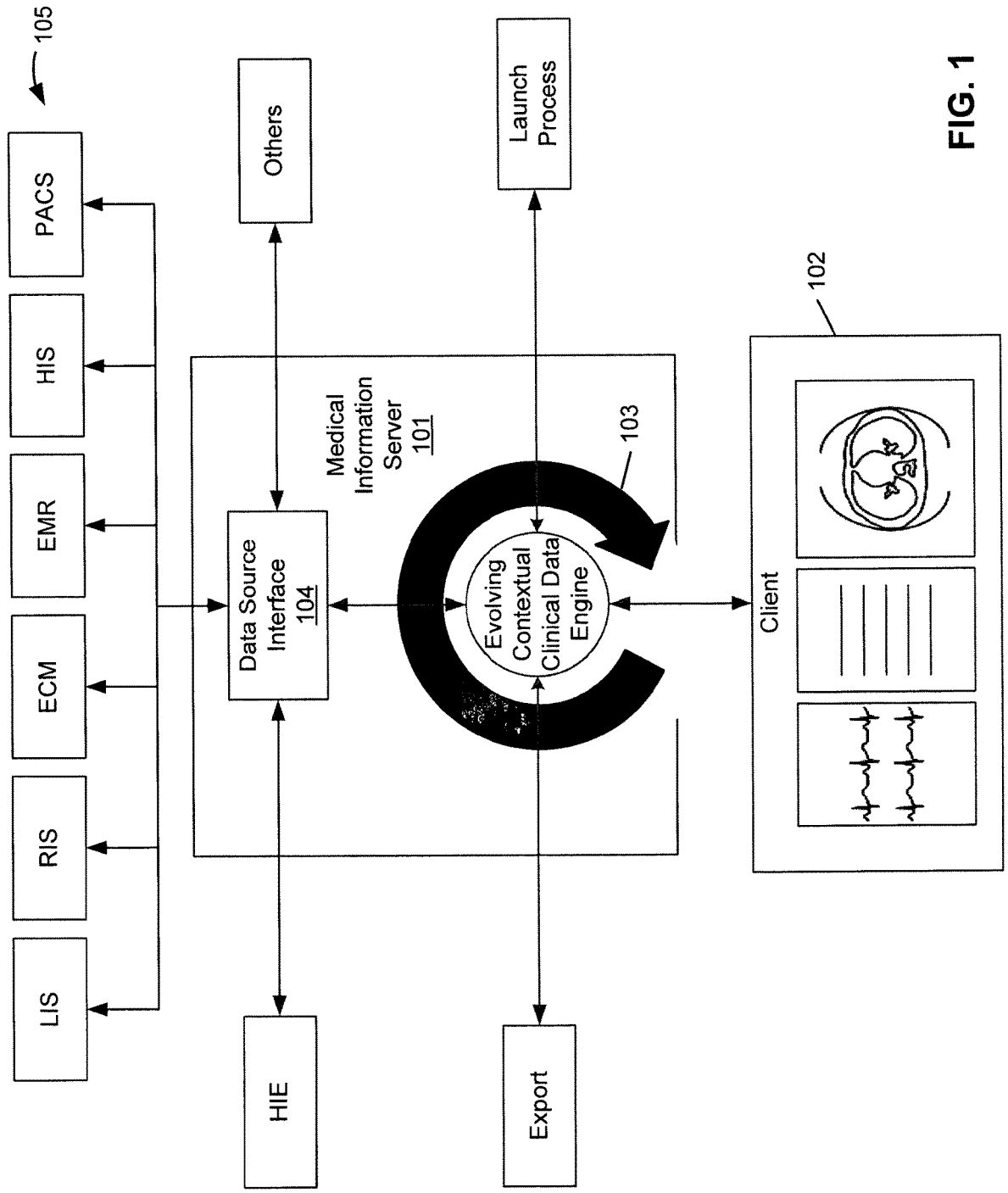
FIG. 1 is a block diagram illustrating a medical information system using Evolving Contextual Clinical Data technology according one embodiment of the invention.

Various embodiments and aspects of the inventions will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment.

According to some embodiments, embodiments of the invention provide for the integrating of medical data using Evolving Contextual Clinical Data technology, including DICOM (digital imaging and communications in medicine) images, non-DICOM images, text, reports, PDF (portable document format) documents, JPEG (joint photographic experts group) files, audio files, video files, office documents, and other data objects, etc. and display of the relevant data to the end user in a useful way, or "in context." "In context" means that the data displayed is relevant to whatever the user is searching. For example, "in context" might mean displaying data relating to a patient ID, accession number, a study ID, login credentials, date, time frame, episode, appointment, body part or area, user, study, insurance code, clinical trial, etc., or any combination of these parameters.

For example, a patient may have had a recent brain scan and want to discuss the results with her physician. The physician would want to view the patient's EMR record, DICOM images of the scan, possibly image processing tools to manipulate the scan images, previous brain scans if available, relevant medications that the patient is taking, relevant lab tests, and relevant reports. The physician would not be interested in weeding through information relating to a broken leg that occurred last year, a pregnancy from 2 years ago, pictures of a skin allergy or other non-relevant information.

According to one embodiment, a medical information server employs an ECCD engine to analyze user past interactions with the medical information presented by the medical information server. Based on the analysis of the user behavioral patterns with respect to different medical information provided by the medical information server, the ECCD engine generates a set of ECCD rules or models specifically tailored to a particular user's behaviors. The ECCD rules or models can be used by the server to predict or determine further related medical information that the user is likely interested in receiving, in addition to the medical information specifically requested by the user. The related medical information and the requested medical information are then retrieved from various data sources and integrated by a data integrator hosted by the server into one or more views of medical information. The views of medical information are then transmitted to a client device to be presented therein to the user. The user interactions with respect to the medical information currently presented can be utilized by the ECCD engine to train or adjust the ECCD rules or models for future prediction or determination. As a result, medical information can be presented to a user in a manner that is most appropriate or desired by the user. In one embodiment, such a medical information server is an integrated medical image processing server that is communicatively coupled to various medical data sources (e.g., medical data servers) to incorporate different or related medical data of a particular patient or patients.

FIG. 1 is a block diagram illustrating a medical information system using Evolving Contextual Clinical Data technology according one embodiment of the invention. Referring to FIG. 1, medical information server 101 is configured to provide medical information to a variety of clients, such as client 102, over a network. In one embodiment, medical information server 101 includes, amongst others, ECCD engine 103 and data collector or integrator 104. ECCD engine 103 may be implemented in a dedicated computing machine. In one embodiment, ECCD engine 103 may be implemented using artificial intelligence (AI) technology.

Referring back to FIG. 1, in one embodiment, ECCD Engine 103 performs several functions, including receiving information from a viewer, based on a user's input; invoking data collector 104 to query multiple data sources 105 for information relating to the information received from client 102; and integrating and transmitting the data received from the multiple data sources 105 to client 102 to be displayed in the viewer, possibly in different display or viewer areas. This process is repeated in an iterative manner so that the user can narrow or broaden his search, and view the results. This is referred to as an iterative query and is driven by the ECCD Engine.

The ECCD engine 103 may determine what types of medical data a user is likely interested in receiving based on a set of ECCD rules or models that may be modeled based on the prior user interactions or behaviors of a particular user, or of more than one user. ECCD engine 103 communicates, via data source interface or interfaces 104, with data sources 105 to retrieve the medical data based on the recommendation from ECCD engine 103. ECCD engine 103 mines data objects from several different data sources and integrates the data objects with each other based on common meta-data such as patient ID, accession number, date, time frame, body part, body area, condition, encounter, procedure, symptom etc.

The ECCD engine 103 uses specific data source interfaces 104 to connect to the various data sources 105. Medical data is pulled from multiple data sources and transmitted to and displayed in client 102, preferably a thin client and more preferably, a web browser. In the example as shown in FIG. 1, data sources 105 include LIS, RIS, ECM, EMR, HIS, PACS, and HIE (health information exchange) servers. However, more or fewer data sources may be applied. Data sources 105 may be managed and/or operated by different organizations than the organization which operates server 101.

In one embodiment, the medical data provided by data sources 105 may include medical image data in a DICOM format, medical image data in a non-DICOM format, scheduling data, registration data, demographic data, prescription data, billing data, insurance data, dictation data, report data, workflow data, EKG data, best practices reference materials, reference materials, training materials, etc. These data may reside in several locations or systems including HIS, RIS, PACS, LIS, ECM, EMR or other systems. The non-DICOM data may be in several formats including A/V, MPEG, WAV, JPG, PDF, Microsoft Office™ formats and other formats.

Generally, data in the PACS will include DICOM data, where data in the HIS, RIS and LIS, ECM, EMR will include non-DICOM data, including both image and non-image data. HIE data includes data available via a health information exchange system. These data generally include data available across different organizations within a region, community or hospital system, and may be DICOM or non-DICOM data. Other data may include any other relevant data, including data in directories on computers, data from mobile devices, etc.

Since the various systems (e.g., LIS, RIS, ECM, EMR, HIS, PACS, etc.) may use different communication standards or protocols, such as DICOM, HL7 (health level seven), XDS, HIE, ORU, etc., ECCD engine 103 uses specific connectors or data source interfaces 104 to access the data in the various systems 105. These connectors are generally hidden from the end user at the viewer level, so that the user does not need to worry about these complexities. However, certain users with the appropriate access credentials are able to configure the connectors via the viewer interface, directly with the ECCD engine 103, or through some other interface. Types of data connectors include, but are not limited to, mobile, EMR plugin API (application programming interface), Web services, Web browser uploads/downloads, HL7, directory scanners, DLL (dynamic link library) APIs, XDS (cross-enterprise document sharing), VNA (vendor neutral archive), indexing servers, etc.

The viewer or client 102 in this embodiment may be a thin client, such as a web browser on a computer, a mobile device application on a mobile device, etc. The viewer may or may not require any software or plug-in download/installation. The viewer may have one or more viewer/viewing areas to display the data collected from the various data sources and integrated and received from server 101. The viewing areas may be in frames and/or tabs within a Web browser. The viewing areas may overlap, or be integrated with each other. The viewing areas may be within one another. Preferably the viewer will have more than one viewing area.

The data resulting from the ECCD engine 103's querying will preferably be shown in the viewer. However, data may also be exported by the ECCD engine 103 for incorporation into a database, report, to integrate with another system etc. The results of the iterative query may also be stored in either the ECCD engine 103 or exported to be stored in another system, or both. The ECCD engine 103 may also launch another process, such as launching another software system, launching a printer to print etc.

Figure 2:
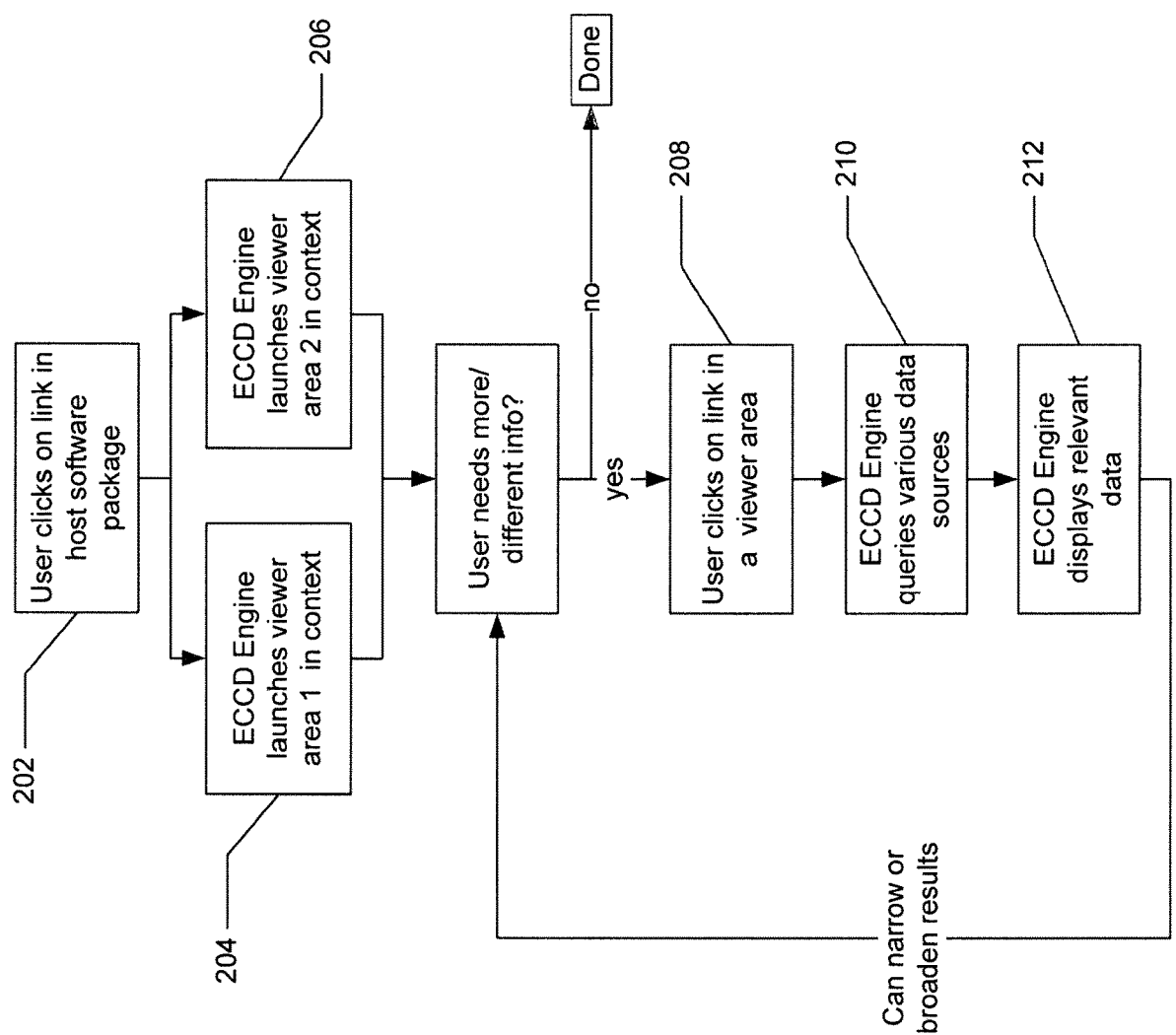
FIG. 2 is a processing flow diagram illustrating how an ECCD engine operates from a client's perspective according to one embodiment of the invention.

FIG. 2 is a processing flow diagram illustrating how an ECCD engine operates from a client's perspective according to one embodiment of the invention. Referring to FIG. 2, at block 202 a user clicks on a link or control (e.g., hypertext link, button, or icon with underlying executable code associated with it) of content displayed by a client software application running at a client device, such as client device 102 of FIG. 1, where content (e.g., medical information) may be provided by medical information server 101 of FIG. 1 over a network (e.g., local area network, wide area network such as Internet, or a combination thereof, wired or wireless) using a variety of communication protocols. A user operating the client device may be a doctor, technician, instructor, patient, or any other user with the appropriate access control credentials to access resources available at medical information server 101. The link may be an image, text, a button, or any other type of link.

The client software application may be an EMR, clinical trial software, imaging software, advanced image processing software or any other type of software. The client software application may be executed as a client in a client-server software environment, or as installed software on a particular computer or mobile or other device. Client software may be a Web browser. For example, the user may click on an HTML (hypertext markup language) link (e.g., text, button, image etc.) which includes the URL (uniform resource locator) of the medical information server as well as identifying information such as patient ID, accession number, body area, date, procedure, or a combination thereof. The embedded information is communicated from client device 102 to the ECCD engine 103 of the medical information server 101 in response to an activation of the link or control by the user.

Boxes 204 and 206 represent the result of the user clicking on a link in the client software application. Box 204 represents the launching of one or more viewer areas in context at client device 102, in response to content information received from medical information server 101, where ECCD engine 103 of server 101 generates the content information based on the user interaction with the link at box 202 using Evolving Contextual Clinical Data technology. In context in this example means that the data displayed in the viewer area are related to the link that the user clicked in the host software and at least some of the data is predicted or determined (although not specifically requested by the user) by the ECCD engine 103 based on one or more ECCD rules or models that are associated with the user and/or the metadata. For example, if the link relates to a CT scan done on a particular date, the viewer area may show the relevant CT scan images. The ECCD engine 103 can determine the context based on metadata in the link. For example, data relating to the patient ID, accession number, a study ID, login credentials, date, body part or area, etc. may be included in the metadata.

Box 206 represents the launching of another viewer area in context. For example, if the link in box 202 relates to a CT scan done on a particular date, the second viewer area may show the notes, report, or dictation relating to the particular CT scan. The ECCD engine 103 can determine the context based on metadata in the link. For example, data relating to the patient ID, accession number, study ID, login credentials, date, body part or area, etc. may be included in the metadata. The information presented in the viewer areas can be pulled from all the data sources (e.g., data sources 105 of FIG. 1) with which the ECCD engine 103 is coupled.

The viewer areas launched by the ECCD engine 103 may be in the same window as the host client software. For example, multiple viewer areas may launch as different frames within a Web browser window, where the Web browser window hosts the host software. However, the viewer areas may also launch in one or more different windows. The viewer areas may also launch into different tabs within the window. The viewer areas may also overlap. The viewer areas may also be integrated with each other, for example showing data from more than one data source in a single frame. The viewing areas may also be within each other, for example, viewing area 1 may be within viewing area 2. The host software system window may also be within a viewing area.

In some situations, the information presented initially in the viewer areas may be adequate for the user. However, if the user wants to narrow or broaden his query to obtain different information, he/she would continue to the step represented in box 208. Box 208 represents a user clicking on a link within a viewer area. The user may click a link to either narrow or broaden the scope of information presented in the viewer areas. For example, the user may click on a link relating to a specific date, or the user may click on a link relating to a specific condition, etc. The user may also submit a specific query such as "show me all data relating to a particular date." The query option may be presented to the user within one of the viewer areas which is displaying data or in a separate viewer area.

Box 210 shows that the ECCD engine 103 queries the various data sources based on the additional inputs provided by the user. Box 212 represents the display of more relevant data in the viewer areas. From here, the user can continue to narrow or broaden the results by clicking on different links within the viewer areas. This querying can be done repeatedly until the user is able to view the information he requires. The ECCD engine 103 can learn from a user's or users' iterative querying to better present relative data "in context" initially in the future by training the ECCD rules or models associated with the user and/or the metadata.

Figure 3:
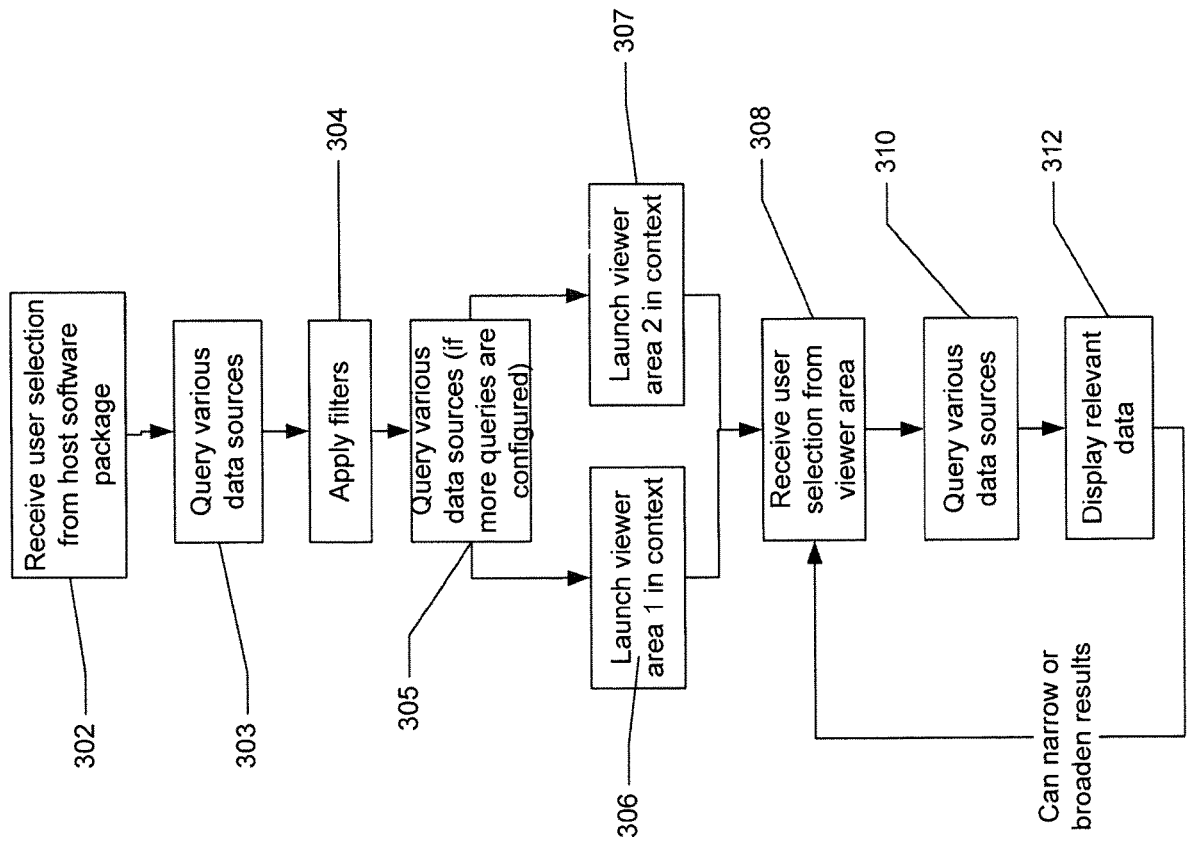
FIG. 3 a processing flow diagram illustrating how an ECCD engine operates from the ECCD engine's perspective according to one embodiment of the invention.

FIG. 3 a processing flow diagram illustrating how an ECCD engine operates from the ECCD engine's perspective according to one embodiment of the invention. Referring to FIG. 3, box 302 represents the ECCD engine 103 receiving information from a user. This information is conveyed by the user clicking a link of some sort in the client software application as shown in box 202. The ECCD engine 103 may also be automatically launched (without the need for a user to click on a link). For example, the ECCD engine 103 may automatically launch for a user every morning to show data relating to new patients. The launching of the ECCD engine 103 spawns the integration and display of multiple data sources in an intelligent manner, or "in context".

Box 303 represents the action that the ECCD engine 103 takes as a result of receiving the information from the user selection in box 302. The ECCD engine 103 queries the various data sources (e.g., data sources 105 of FIG. 1) to find the data which is most relevant to the user selection. Box 304 represents any data filters that are applied to the data. For example, a user may have configured certain filters to only present certain types of data, for example only images or only data relating to a certain time frame. The ECCD engine 103 may have its own filters such as those "learned" by past user behavior. For example, the ECCD engine 103 may have "learned" that a particular user usually wants to see EKG data next to any CT scan data of the chest area. Such "learned" information may be compiled into the updated ECCD rules or models for future uses. In this case, if the user has clicked on a link in the host software package which indicates a CT scan of the chest, the ECCD engine 103 will know, based on the ECCD rules or models, to also present this user with EKG data.

Figure 4:
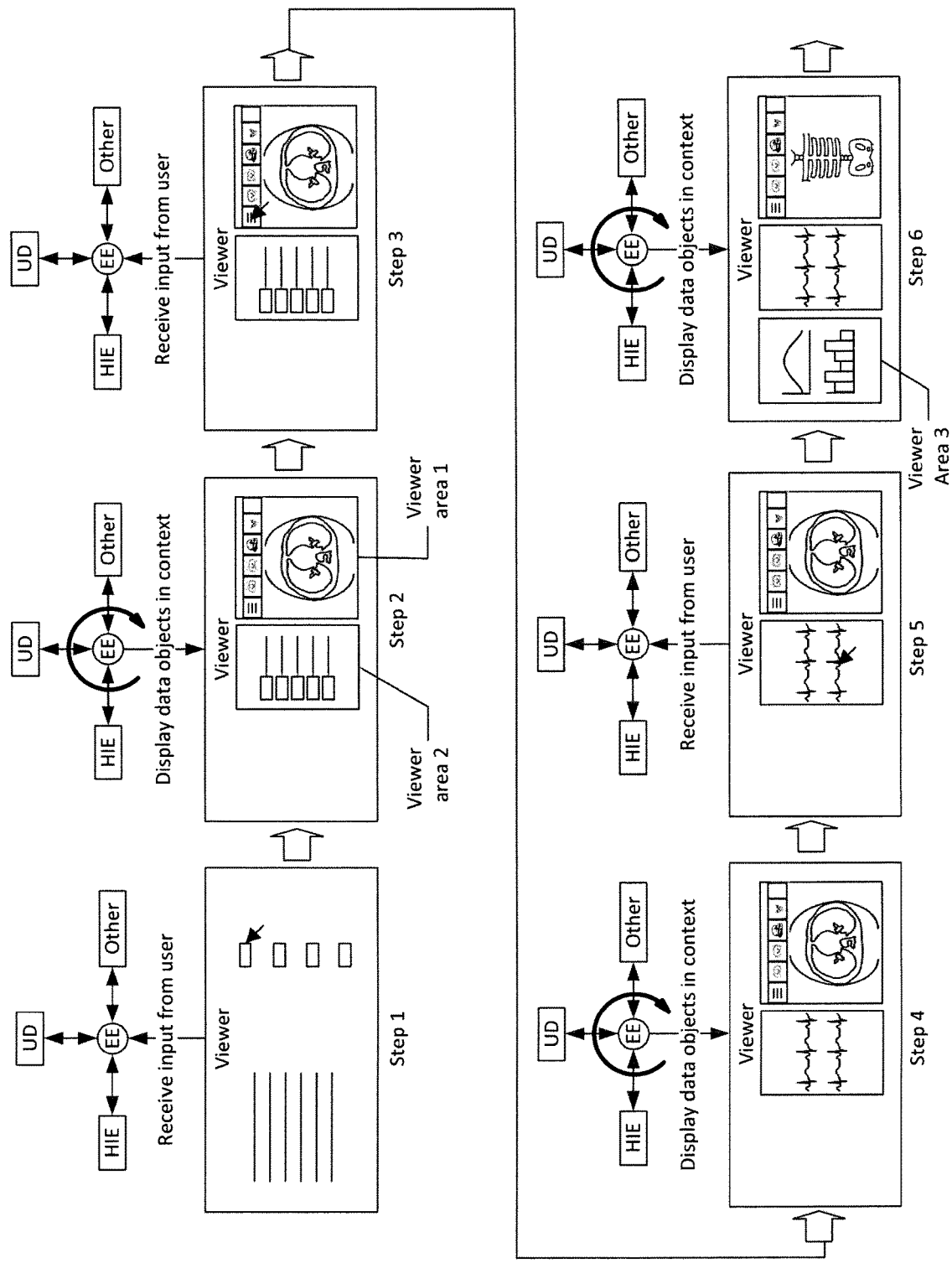
FIG. 4 shows the interaction between an ECCD engine and a client/viewer user interface according to certain embodiments of the invention.

Box 305 represents another data source query by the ECCD engine 103. This additional query may only take place if the user has configured multiple query levels for the system to perform automatically. For example these iterations may be configured in a screen as shown in FIG. 4. This additional automatic query is one way that the ECCD engine 103 can conduct an iterative query. The user may also conduct an iterative query manually via blocks 208-212, also represented in blocks 308-312.

Box 306 represents the ECCD engine 103 launching a viewer area in context. In context in this example means that the data displayed in the viewer area are related to the link that the user clicked in the host software. For example, if the link relates to a CT scan done on a particular date, the image viewer area may show the relevant CT scan images. The ECCD engine 103 can determine the context based on meta-data in the link. For example, data relating to the patient ID, accession number, study ID, login credentials, date, time frame, episode, appointment, body part or area, user, study, insurance code, clinical trial, etc. may be included in the meta-data.

Box 307 represents the ECCD engine 103 launching another viewer area in context. For example, if the link relates to a CT scan done on a particular date, the second viewer area may display the notes, report, or dictation relating to the particular CT scan. The ECCD engine can determine the context based on metadata in the link. For example, data relating to the patient ID, accession number, study ID, login credentials, date, body part or area, etc. may be included in the meta-data. The information presented in the second viewer area can be pulled from all the data sources with which the ECCD engine 103 is coupled.

If the user has the information he/she needs at this point, and does not need to get different/more information, the workflow would stop here. If the user wants to change his/her query and view different information, the workflow will continue on to box 308. Box 308 represents the ECCD engine 103 receiving information relating to a link clicked by the user in one of the viewer areas, as shown in box 208. In response to receiving this information, the ECCD engine runs another query of the data from the various data sources to which it is connected (box 310) using the information embedded in the new query and displays the narrowed or broadened information in the viewer areas (box 312). The configuration of "in context" can be done by a user with the proper access credentials. This configuration could be performed via the viewer client interface, a different client interface, or directly at the ECCD engine server.

FIG. 4 shows the interaction between an ECCD engine and a client/viewer user interface according to certain embodiments of the invention. The steps shown represent possible steps, as examples for the illustration purpose only, that a user might take to view and interact with the information presented by the ECCD engine 103. The activity of the ECCD engine 103 is also represented in FIG. 4. Referring to FIG. 4, step 1 shows the host software (e.g., client software) in the viewer, or client screen. Within the host software there may be links that when selected, or clicked, communicate with the ECCD engine 103 and send the ECCD engine 103 information, such as a patient ID, accession number, study ID, login credentials, date, body part or area, etc. Step 1 shows a pointer selecting a link and the information from the link being transferred to the ECCD engine 103 (also referred to "EE" in this diagram). The diagram also show that the ECCD engine 103 is connected to various data sources, including HIE, unstructured data ("UD" in this diagram) and possibly other data, as described above.

Step 2 shows what happens after the ECCD engine 103 receives the input from the user. The ECCD engine 103 queries the various data sources to find and retrieve data relevant to the information sent by the user to the ECCD engine 103. For example, the user may have clicked on a link that conveyed information including the patient ID and a date to the ECCD engine 103. The ECCD engine 103 would query all the relevant data sources for information relating to that patient ID and that date and transfer this information back to the viewer. Depending on the format of the information, the viewer may launch different viewing areas, such as a DICOM viewing area and a non-DICOM viewing area. Viewing areas may be able to accommodate data of many different formats including DICOM images, non-DICOM images, text, reports, PDFs, JPEGs, audio files, video files, office documents (Microsoft, etc.), etc. Preferably at least 2 viewing areas are launched to show the related information, but more viewing areas may be launched. Viewing areas may show up within the host viewer, in frames, as tabs, as separate windows, as separate frames etc. Viewing areas may be floating on top of one another, in separate windows or pop-up windows. Viewing areas may be on separate monitors. Viewing areas may be integrated with the host application and/or other software applications in any of the same formats mentioned here. Viewing areas may be integrated into more than one software application simultaneously.

Step 3 shows a user using a pointer (key strokes, interactive voice commands, or a combination thereof) to click on a link within one of the viewing areas. The clicking of this link again sends specific information or request to the ECCD engine 103. For example, there may be several CT scans shown in a DICOM image viewer area, and the information displayed in another viewing area may relate to these multiple CT scans. The user may want to narrow the data to those related to only one CT scan. By clicking on the single scan date, the user conveys this date information (as well as other information) to the ECCD engine 103.

Step 4 shows the ECCD engine again querying the various data sources for information relating to the new request conveyed by the user. As a result of the query, the ECCD engine 103 transmits different information to the client device to be displayed in at least one viewer area in the viewer. Step 5 shows the user again clicking on a link in one of the viewer areas to narrow or broaden the information displayed. Step 6 shows the ECCD engine 103 launching a third viewing area. Although the third viewing area is shown here side by side in the same window as the other 2 viewing areas, viewing areas may be shown in tabs, in separate windows, overlapping, integrated etc. Note that the information displayed in at least some of the viewing areas changes as the user submits more information to the ECCD engine 103. A third viewing area is shown in this example, but the new information may also be launched in one of the 2 viewing areas shown in steps 2-5.

FIG. 4 shows the iterative process based on the user interaction within the various viewing areas. It should be appreciated that the ECCD engine can learn from a user's habits and from users' habits in general. The users' clicks and preferences create data which is added to the meta-data of the various data objects and/or may be added to the logic/rules of the ECCD engine itself. The ECCD engine 103 can then use this information to better present data in context, for example, by training the corresponding ECCD rules or models associated with the user. As a result, the ECCD engine 103 can present information to the user with fewer "clicks" over time.

Figure 5:
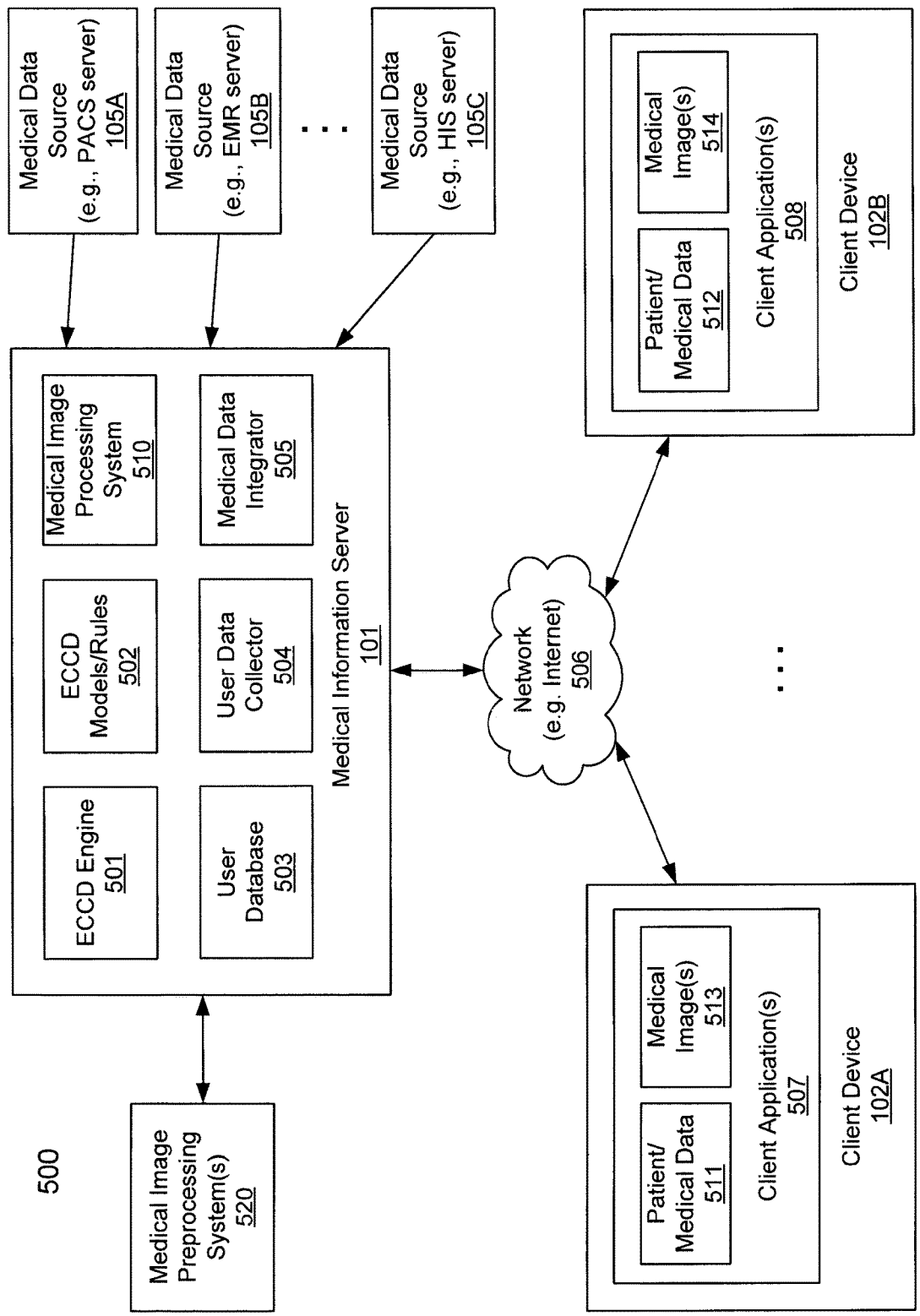
FIG. 5 is a block diagram illustrating a medical information system according to one embodiment of the invention.

FIG. 5 is a block diagram illustrating a medical information system according to one embodiment of the invention. For example, system 500 may represent the system as shown in FIG. 1, where at least some of the components of server 101, such as ECCD engine 501 and ECCD rules/models 502, may be implemented as part of ECCD engine 103. Referring to FIG. 5, system 500 includes, but is not limited to, one or more clients 102A-102B communicatively coupled to medical information server 101 over network 506. Network 506 may be a local area network (LAN), a metropolitan area network (MAN), a wide area network (WAN) such as the Internet or an intranet, a private cloud network, a public cloud network, or a combination thereof.

In one embodiment, medical information server 101 hosts therein, amongst others, ECCD engine 501, ECCD models/rules 502, user database(s) 503, user data collector 504, medical data integrator 505, and medical image processing system 510. ECCD engine 501 may be implemented using a variety of technologies available to model and generate ECCD rules or models 502 based on user interactions, behaviors, and/or user preferences of a particular user stored in user database 503. The user interactions may be monitored and captured by user data collector 504, which monitors user interactions of client software applications 507-508 at clients 102A-102B. The captured user interactions may then be stored in user database 503 and analyzed by ECCD engine 501 to generate ECCD rules or models 502.

According to one embodiment, when a user of a client, in this example, a user of client 102A, interacts with content (e.g., patient or medical data 511, medical image 513) presented at client software 507 (e.g., client application, Web browser), a signal or message representing the user interaction (e.g., click, keystroke, voice command) is transmitted by client application 507 to medical information server 101. The message may include the specific content the user has interacted with, as well as other metadata (e.g., patient ID, body area, medical procedure ID, medical appointment, medical condition, user ID, date and time of the interaction, etc.) Based on the message received from client 102A, data integrator 505 invokes ECCD engine 501 and/or ECCD rules/models 502 to determine a set of medical data. The ECCD rules/model 502 may be identified based on a user ID of the user operating client software 507 and/or metadata. Based on the determined data set, data integrator 505 identifies some of the data sources 105A-105C that are able to provide such data. Data integrator 505 communicates with the identified data sources 105A-105C to retrieve the medical data determined or recommended by ECCD engine 501 and/or ECCD rules/models 502.

Data integrator 505 integrates the retrieved medical data into one or more views of medical information. In one embodiment, data integrator 505 integrates the medical data in a manner that is most appropriate for the user, for example, based on the ECCD rules/models 502 associated with the user. The one or more views of the medical information are then transmitted from medical information server 101 to client 102A over network 506 and presented to the user by client software application 507 as part of medical data 511 and/or medical images 513. Note that the presented medical information may include the medical information requested by the user when the user interacted with the content previously presented. In addition, the medical information may further include information that is not specifically requested by the user, but is recommended by the ECCD engine 501 based on ECCD rules/models 502. For example, when a user requests information concerning a CT scan, based on the ECCD rules or models associated with the user, the ECCD engine may recommend, for example, based on another set of ECCD rules that is associated with the metadata of the CT scan, that one or more lab tests, or an EKG, associated with the CT scan may also be presented to the user. Although the user did not specifically request the lab tests nor EKG, however, based on the ECCD rules or models, the user may be more likely interested in receiving the lab tests or EKG when viewing the CT scan information.

Medical images 513 may be rendered or generated by image processing system 510, which may be integrated within medical information server 101 or remotely as part of image processing system 520 hosted by a separate server or cluster of servers. Various data sources 105A-105C may be hosted by one or more servers, which may be operated by the same or different organizations. In one embodiment, data sources 105A-105C include LIS, RIS, ECM, EMR, HIS, PACS, and HIE servers. Data integrator 505 communicates with data sources 105A-105C to retrieve medical data using a variety of communication methods or protocols, such as, for example, DICOM, HL7, XDS, HIE, and ORU, etc.

Figure 6:
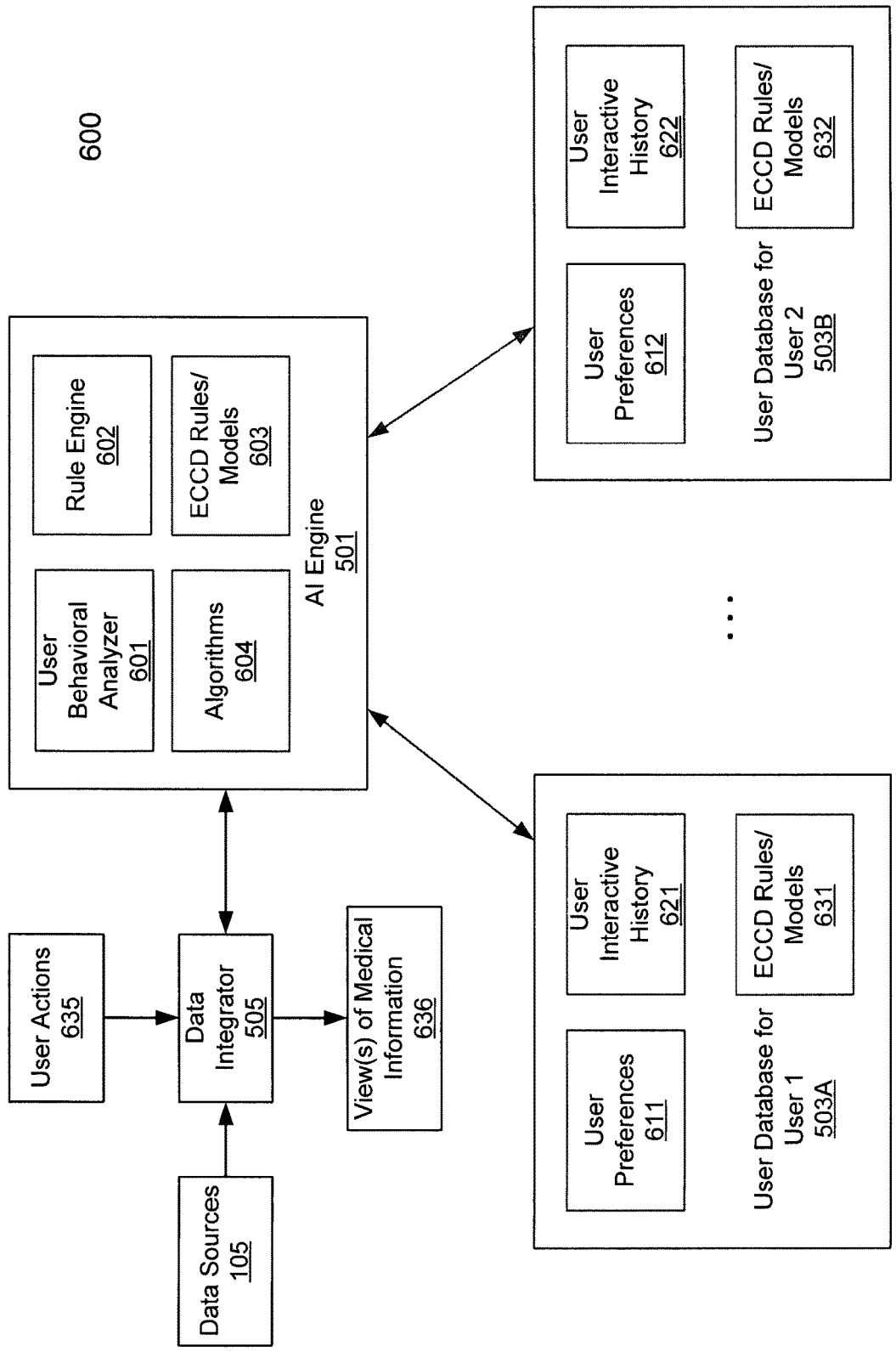
FIG. 6 is a block diagram illustrating an Evolving Contextual Clinical Data engine for processing medical information according to one embodiment of the invention.

FIG. 6 is a block diagram illustrating an Evolving Contextual Clinical Data engine for processing medical information according to one embodiment of the invention. Referring to FIG. 6, system 600 may be implemented as part of medical information server 101 of FIG. 5. In one embodiment, ECCD engine 501 includes, but is not limited to, user behavioral analyzer 601, rule engine 602, and ECCD rules or models generated by ECCD engine 602. In one embodiment, user behavioral analyzer 601 analyzes user interactive data of a user to determine user behavioral patterns with respect to accessing different medical information of a patient. For example, user behavioral analyzer 601 may access user databases 503A-503B of different users to analyze user interaction histories 621-622 of the corresponding users to determine their respective behavioral patterns. The user interaction histories 621-622 may be collected by user data collector 504 of FIG. 5 and stored in the user databases 503A-503B, which may be implemented in one or more databases in a persistent storage device such as hard drives. The user behavioral patterns may be determined or modeled using a variety of algorithms or technologies 604, as described above. User behavioral patterns may be used for that individual user or aggregated across more than one user.

Based on the user behavioral patterns determined by user behavioral analyzer 601, rule engine 602 compiles and generates a set of ECCD rules or models 603 for each of the users based on their respective behaviors and personal preferences (e.g., user preferences 611-612). The ECCD rules and/or models are then stored in the corresponding user databases as part of ECCD rules/models 631-632 or alternatively, they may be centrally maintained by ECCD engine 501 as part of ECCD rules/models 603. Subsequently, when a new user action 635 is received for accessing certain medical data, data integrator 505 invokes ECCD engine 501 to access ECCD rules/models 603 and/or ECCD rules/models 631-632 corresponding to the user to determine additional medical data. Data integrator 505 then communicates with the associated data sources 105 to retrieve the requested medical data (e.g., first medical data) and the additional medical data (e.g., second medical data). The retrieved medical data is then integrated by data integrator 505 to generate one or more views of medical information 636. The one or more views of medical information 636 is then transmitted to a client device of the user to be presented therein.

Furthermore, the user action 635 may be captured and stored in a persistent device as part of user interaction history (e.g., user interaction histories 621-622). The updated user interaction history may be used or "learned" by ECCD engine 501 to train or adjust the corresponding ECCD rules or models for future use. For example, if users rarely or never request EKG data when viewing scans of the brain, then the ECCD engine 501 will learn, by configuring the corresponding ECCD rules or models, not to present the EKG data when a user is viewing a scan of the brain. In this situation, the user may need to make a specific query to view the EKG information if he/she wants to, and such a user action may trigger further modification of its ECCD rules or models.

In another example, based on the past user behaviors, a user may always want to view images representing an EKG of a patient when he is viewing a CT scan of the chest area, as a cardiologist might. Once t user has made this request one or more times, the ECCD engine 501 can learn that this user frequently desires viewing these images at the same time, and ECCD engine 501 may modify the ECCD rules/models to present the EKG data when the user subsequently requests the viewing of a CT scan of the chest area. If many other users also frequently request the EKG data while viewing CT scans of the chest area, the ECCD engine 501 can interpret this data and raise the likelihood of presenting the EKG data when chest CT scan data is requested for all users, or a subset of all users, for example, cardiologists. In this way, the ECCD engine 501 is able to "learn" what "in context" means for different users or different types of users or all users.

Another way that the ECCD engine 501 may learn from its users is by tracking click through rates and view times (e.g., monitored by user data collector 504 of FIG. 5) and by connecting this information within the ECCD engine 501 with the user, type of study, individual study, type of information, other information being displayed, etc. A shorter click through rate and/or a shorter viewing time may indicate less relevant information while a longer click through rate and/or a longer viewing time may indicate more relevant information. Using this collected information over time, the ECCD engine 501 grows more intelligent as it is used by refining the content it presents. For example, a user or users may view lab data which is older than 3 months for only a few seconds, but view newer lab data for much longer, indicating that the older information is not very useful. Using this information, the ECCD engine 501 may, in this example, become less likely to present lab data more than 3 months old to a user or users.

Another example of how the ECCD engine 501 may learn from its users is by tracking total interpretation time. Total interpretation time may be the time to view multiple related images or information objects, and/or it may be the time to perform certain advanced image processing steps, and/or may be the total time reviewing information relating to a single patient. This information can be analyzed by the ECCD engine 501 to determine trends in reading times. This information can ultimately be used to reduce total reading times. For example, if the ECCD engine 501 determines that a physician spends 30 minutes reviewing a particular patient when part of the review process includes viewing a CT scan by itself, but only 10 minutes reviewing a patient when a CT scan is presented next to a prior CT scan, the system may increase the likelihood that it will display older or newer CT scans when the user chooses a CT scan to view.

Another example of how the ECCD engine 501 may learn from its users is by directly requesting user feedback. For example, the ECCD engine 501 may ask if displaying certain data objects has been useful or not useful. By collecting and analyzing this information, the ECCD engine 501 can more quickly learn what data objects are more or less relevant. The ECCD engine 501 also knows the combination of data objects it is displaying at any given time and can incorporate this knowledge into the analysis. For example, if users indicate that an EKG is not very useful when displayed by itself, or in conjunction with a colonoscopy, but indicate that an EKG is very useful when displayed along aide a CT scan of a heart, the ECCD engine 501 will learn to display the EKG more often when a CT scan of a heart is being viewed, and possibly less often otherwise. The above examples are just few of possible situations, which may be represented by ECCD rules/models 603 and 631-632. Other possibilities can also be applied.

Figure 7:
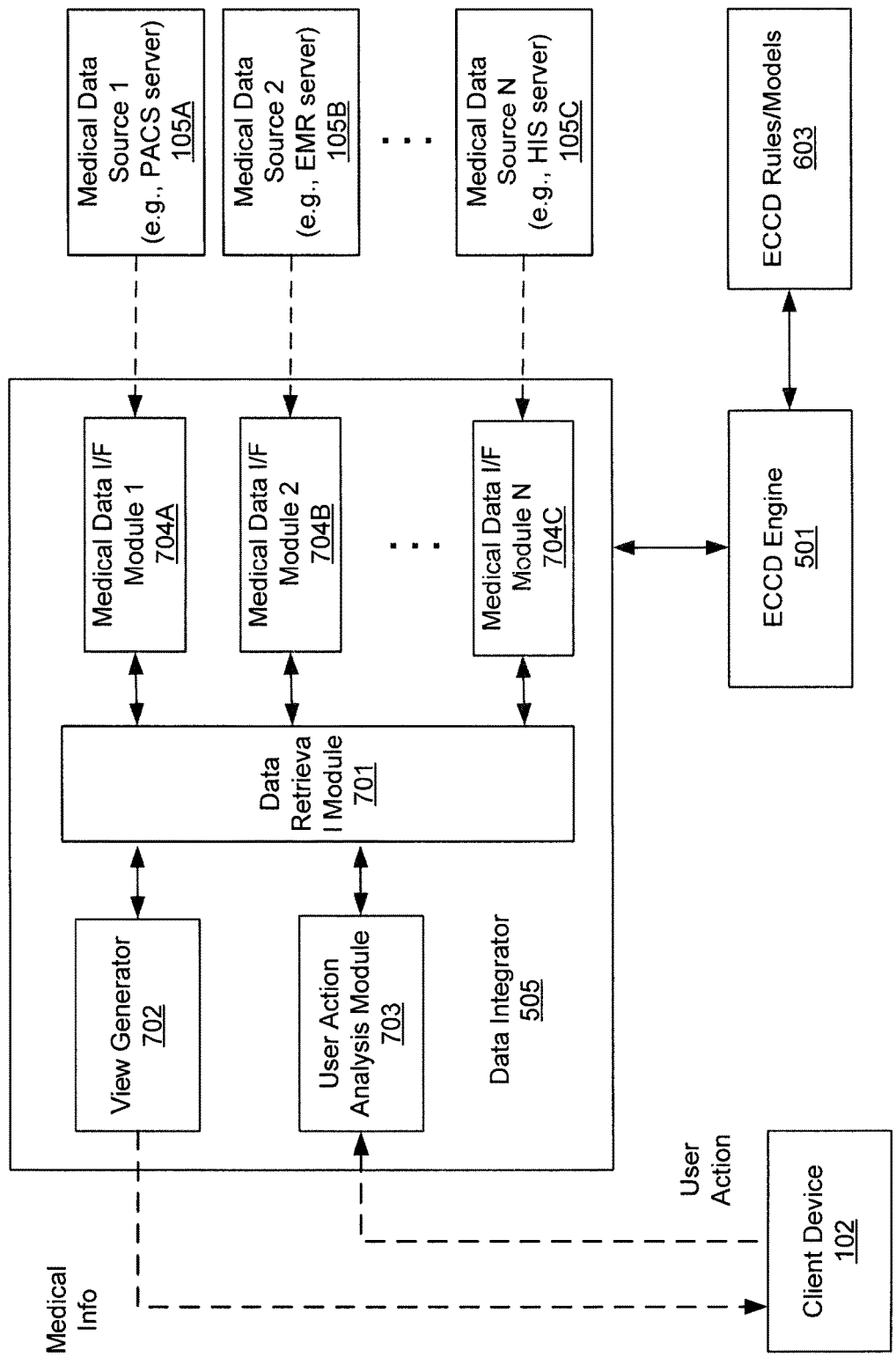
FIG. 7 is a block diagram illustrating an example of a data collector of a medical information server according to one embodiment of the invention.

FIG. 7 is a block diagram illustrating an example of a data collector of a medical information server according to one embodiment of the invention. Referring to FIG. 7, data integrator 505 includes, but is not limited to, data retrieval module 701, view generator 702, user action analysis module 703, and medical data interface (I/F) modules 704A-704C. According to one embodiment, when a user interacts with medical content presented by client device 102, a signal or message is transmitted from client device 102 to medical information server 101 over a network and such signal or message is received by user action analysis module 703. The received message may include certain metadata indicating what content item the user interacted with and other identifying information (e.g., user ID, patient ID, medical procedure ID, body area or body part ID, date and/or time of the interaction, medical condition ID, medical appointment ID, etc.) User action analysis module 703 extracts the information from the message and performs an analysis on the extracted information.

In one embodiment, based on the analysis, user action analysis module 703 invokes ECCD engine 501 by providing the information of the results of analysis and/or the extracted metadata from the message. In response, ECCD engine 501 identifies a set of ECCD rules or models from ECCD rules/models 603 that is associated with the user of client device 102, for example, based on a user ID of the user. ECCD engine 501 then derives a set of one or more actions or recommendations based on the inputs provided by user action analysis module 703 using the corresponding ECCD rules or models associated with the user. The recommendations may include certain additional medical data that is related to the medical data requested by the user, where the additional medical data may be envisioned or predicted by ECCD engine 501 that the user is likely interested in receiving in view of the requested medical data and/or the user action extracted from the message received from client device 102.

Based on the first medical data originally requested by the user and the second medical data additionally recommended by ECCD engine 501, data retrieval module 701 identifies one or more of data sources 105A-105C that provide such medical data. For example, data retrieval module 701 may determine the identifiers for different medical data requested by the user and those recommended by ECCD engine 501. Data retrieve module 701 may maintain and/or access a database or data structure that maps the medical data identifiers to the corresponding data sources. Based on the identified data sources, data retrieval module 701 invokes or calls corresponding medical data interface modules 704A-704C, which in turn access the data sources 105A-105C, respectively.

Medical data interface modules 704A-704C include interface logic (either in software, hardware, or a combination of both) that is specifically designed to handle communications with a specific one of data sources 105A-105C. Each of data interface modules 704A-704C includes functionalities that are specifically configured to communicate with a corresponding one or more of data sources 105A-105C, using specific communication protocols (e.g., TCP/IP, DICOM, HL7, XDS, HIE, ORU, etc.) or application programming interfaces (APIs) that are compatible with or recognized by the corresponding data source. This includes proper protocol signaling or calling convention, handshaking, data exchange, and authentication of different users using associated authentication credentials.

According to one embodiment, data interface modules 704A-704C may also reformat the medical data (e.g., raw data) received from data sources 105A-105C to a format common to or expected by data retrieval module 701 or alternatively, data retrieval module 701 may handle the reformatting operation. In one embodiment, each of data interface modules 704A-704C includes a plugin interface module for the corresponding data source. Data interface modules 704A-704C can handle different types of data, such as, for example, DICOM images, non-DICOM images, text, reports, PDF documents, JPEG files, audio files, video files, office documents, and other data objects. Data sources 105A-105C may be hosted by a variety of servers or clusters of servers, including LIS, RIS, ECM, EMR, HIS, PACS, and/or HIE servers.

Once the medical data has been retrieved by data retrieval module 701 from data sources 105A-105C, the medical data is integrated by view generator 702 to generate one or more views of medical information. The one or more views of medical information may be arranged according to a layout preferred by the user based on the user preferences. Alternatively, views of medical information may be formulated in a manner recommended by ECCD engine 501 based on the ECCD rules or models 603, and/or further in view of the user preferences. For example, less frequently used image processing tools may not be presented to the user or presented at a lower priority with respect to other more frequently used image processing tools, etc. The one or more views of medical information are then transmitted to client device 102 to be presented therein. If the user further interacts with the medical information, the user interaction is captured again and sent to data integrator 505, and the above processes are iteratively performed.

Figure 8:
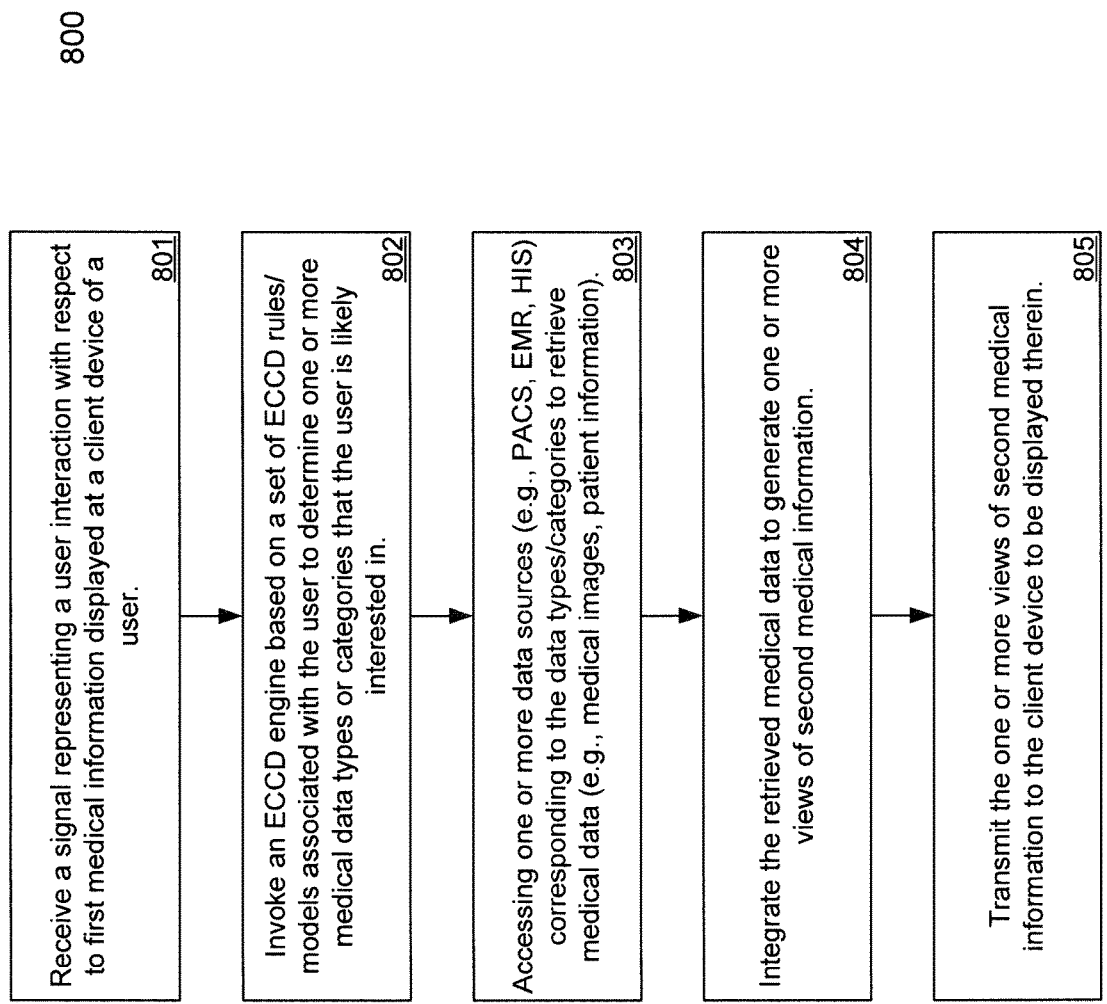
FIG. 8 is a flow diagram illustrating a process for processing medical data using Evolving Contextual Clinical Data technology according to one embodiment of the invention.

FIG. 8 is a flow diagram illustrating a process for processing medical data using Evolving Contextual Clinical Data technology according to one embodiment of the invention. Process 800 may be performed by processing logic, which may include software, hardware, or a combination thereof. For example, process 800 may be performed by medical information server 101 and particularly, process 800 may be performed by data integrator 505. Referring to FIG. 8, at block 801, processing logic receives a signal or message presenting a user interaction with respect to medical information (e.g., first medical information) displayed at a client device of a user. At block 802, processing logic invokes an ECCD engine based on a set of ECCD rules or models associated with the user to determine medical data that the user is likely interested in receiving, in addition to the medical data requested by the user. The ECCD rules or models may be generated by the ECCD engine based on prior user interaction or behaviors of the user. The ECCD rules or models are periodically trained or adjusted based on recent user interactions.

At block 803, based on the medical data requested by the user, as well as determined by the ECCD engine, the data sources corresponding to the medical data are identified and accessed to retrieve the medical data. At block 804, the retrieved medical data is integrated into one or more views of medical information (e.g., second medical information). At block 805, the views of medical information are then transmitted to the client device to be presented to the user. When the user further interacts with the views of medical information, the user interaction is captured again and received by the server, and the above processes may be iteratively performed.

Figure 9:
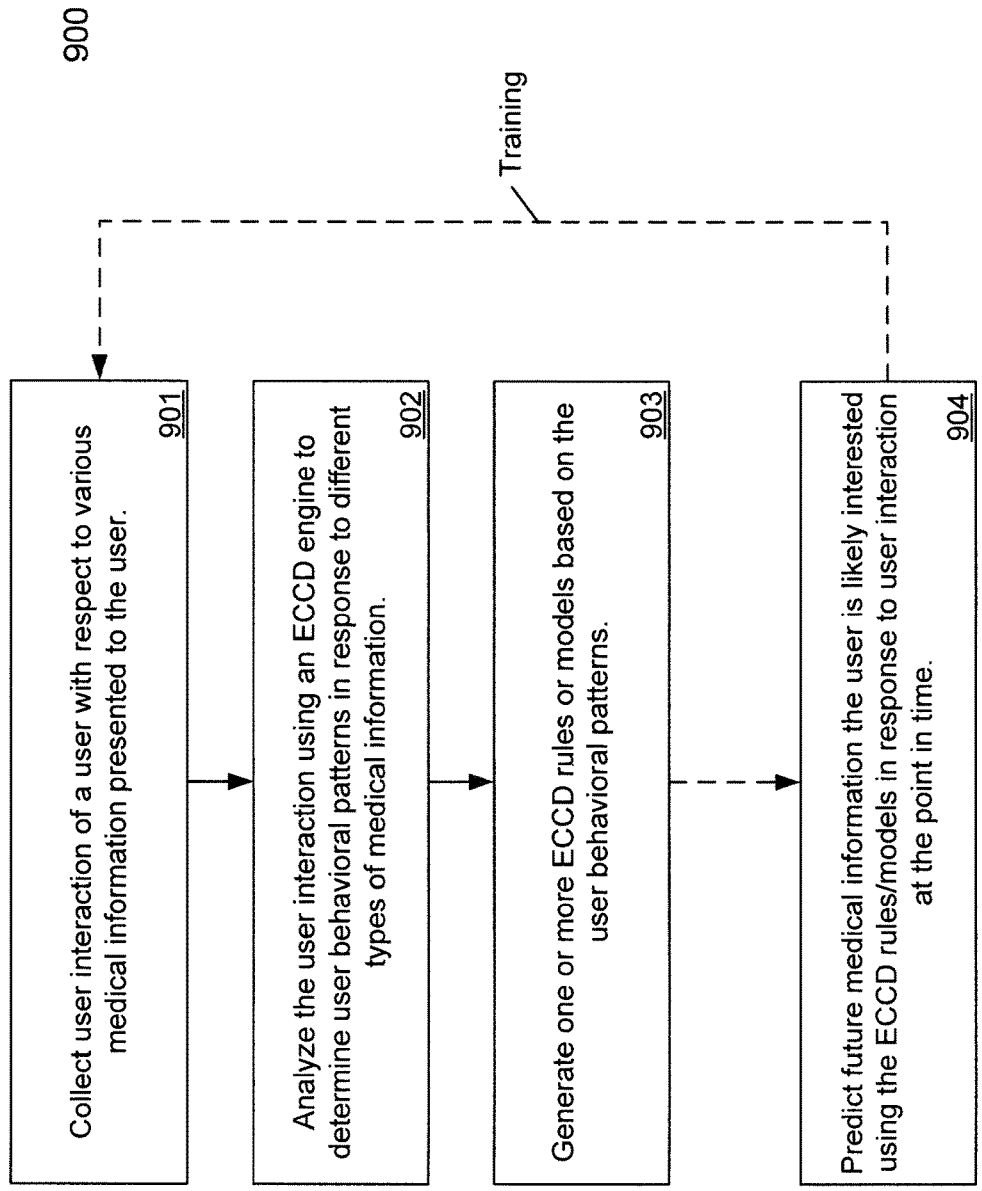
FIG. 9 is a flow diagram illustrating a process for processing medical data using Evolving Contextual Clinical Data technology according to one embodiment of the invention.

FIG. 9 is a flow diagram illustrating a process for processing medical data using Evolving Contextual Clinical Data technology according to one embodiment of the invention. Process 900 may be performed by processing logic, which may include software, hardware, or a combination thereof. For example, process 900 may be performed by medical information server 101 and particularly, process 800 may be performed by ECCD engine 501. Referring to FIG. 9, at block 901, processing logic monitors and collects user interactions of a user with respect to various medical information presented to the user. At block 902, the user interactions are analyzed using Evolving Contextual Clinical Data technology to determine user behavioral patterns in response to different types of medical information. At block 903, one or more ECCD rules or models are generated based on the user behavioral patterns. Subsequently at block 904, the ECCD rules or models are utilized to predict future medical information the user is likely interested in receiving. The newly received user interactions may be captured and used to train or adjust the ECCD rules or models. Although FIG. 9 depicts rules or models based on a single user's behavioral patterns, it will be appreciated that rules or models may also be formed using more than one user's behavioral patterns, or in other words, based on aggregate user activity.

FIGS. 10A-10F are screenshots illustrating examples of graphical user interfaces for providing medical information according to some embodiments of the invention. GUIs as shown in FIGS. 10A-10F may be generated by medical information server 101 (e.g., view generator 702) and received and presented by a client application (e.g., a viewer program such as a Web browser) executed at a client device (e.g., client device 102). User interactions with displayed content presented by the GUIs are captured and transmitted from the client device to medical information server 101. The user interactions are then interpreted by medical information server 101, for example, by invoking ECCD engine 501 and a set of ECCD rules or models associated with the user operating the client device. In response to the user interaction, medical information server 101 performs proper actions, such as, image processing operations, information retrieval operations, and data processing and/or integration operations, based on the decision or recommendation of ECCD engine 501. One or more views of medical information are generated and returned from medical information server 101 back to the client device. The processing results are presented and/or integrated with the existing information at a display device of the client device.

Figure 10A:
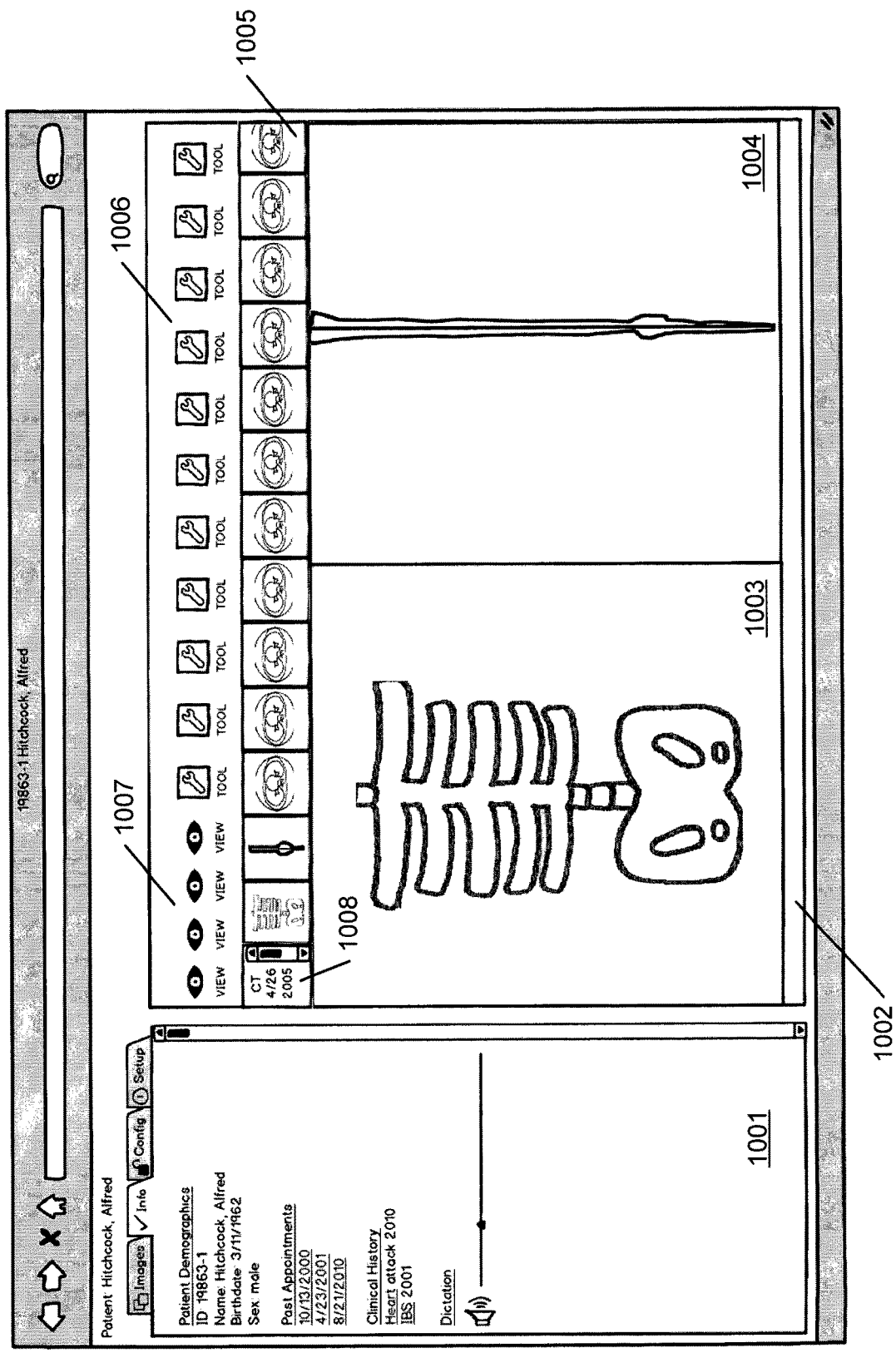
FIGS. 10A-10F are screenshots illustrating examples of graphical user interfaces for providing medical information according to some embodiments of the invention.

Referring to FIG. 10A, in this example, the GUI represents a possible viewer configuration with multiple viewing areas. In this example, the viewer is a Web browser and the viewing areas may be in frames, tabs, or both. In one embodiment, the GUI page as shown in FIG. 10A includes multiple viewing areas, in this example, viewing area 1001 and viewing area 1002. The viewing area 1002 is a DICOM viewing area, where viewing area 1001 shows non-DICOM data in multiple tabs, including in this example, "images" tab, "info" tab, "config" tab, and "set up" tab. The DICOM and non-DICOM data in the viewing areas 1001-1002 have been provided by the ECCD engine as described above. The "info" tab in the viewing area 1001 is selected in this example and shows demographic, appointment, clinical history and dictation data of a particular patient. The patient ID or name is also displayed.

In one embodiment, the DICOM viewing area 1002 includes several images, in this example, image 1003 and image 1004, from one or more image series 1005, as well as several image processing tools 1006 and viewing options 1007. The availability and/or order or priority of the image processing tools may be determined by the ECCD engine as described above. There is also a small scrolling window which shows other CT scan series dates 1008 for this patient, as well as one or more display spaces which display enlarged images for closer viewing. When a user selects any one or more of reduced resolution images or thumbnails 1005, a corresponding enlarged image is displayed in viewing area 1002. In this example, it is assumed the user has selected two thumbnails from thumbnails 1005 and they are displayed in display areas 1003-1004 of viewing area 1002. The multiple viewer areas are related to each other or "in context". For example all of the information displayed may relate to a particular patient's event, such as a heart attack, or the information displayed may relate to a particular patient during a particular time frame, or related to a particular appointment. Such information may be determined and/or recommended by the ECCD engine as described above.

The available tools 1006 may be advanced image processing tools, a list of which is included later in this document. The display of tools may be limited by the ECCD engine to only tools which are relevant to the images being displayed in the viewing area. For example, if the images represent the colon, it is possible for the ECCD engine to only display virtual colonoscopy and/or other relevant tools in this viewing area. The user may click on links in any of the viewer areas to alter the information that the ECCD engine displays. For example, the user may click on an appointment date, or a clinical area in viewing area 1001, or the user may click on an image, a particular area of an image, or a particular image series in the viewing area 1002. The user interaction is then captured and transmitted to the medical information server 101, where the user interaction is processed, for example, using ECCD engine 501 in view of a set of ECCD rules or models associated with the user. Further medical information may be determined as a result and transmitted from the medical information server back to the client device.

Figure 10B:
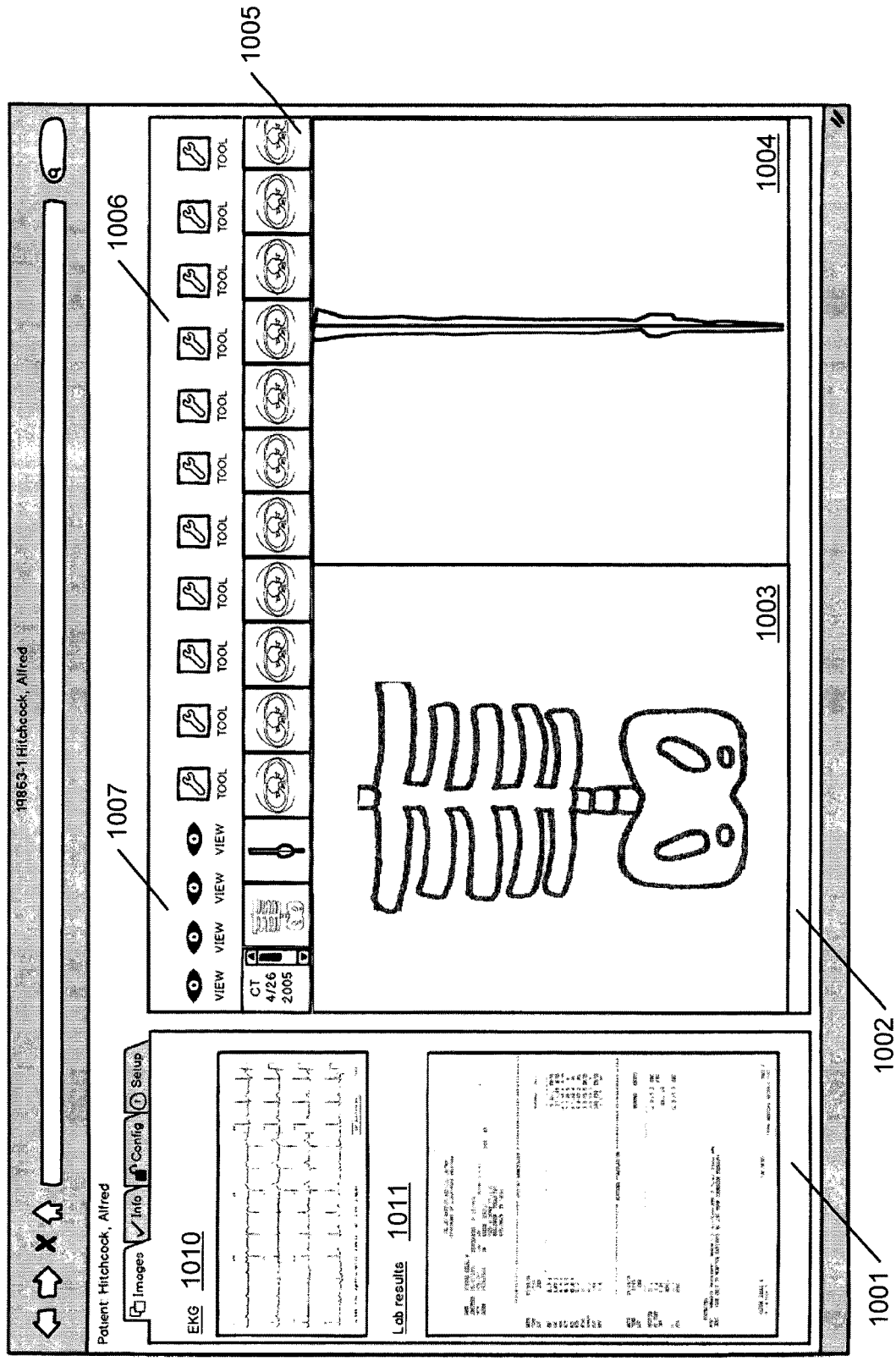

FIG. 10B shows another example of a viewer where the "images" tab in viewing area 1001 has been chosen and non-DICOM images are displayed. In this example, an EKG 1010 and a lab result report 1011 are shown in viewing area 1001. Again, these images are "in context" which means they relate to the patient and/or the images shown in the right viewing area. For example, the DICOM and non-DICOM images shown in FIG. 10A may relate to a heart condition of a particular patient, which may be described in EKG 1010 and lab report 1011 displayed in viewing area 1001. The non-DICOM images shown may also be clickable, or linked to communicate with the ECCD engine as with the other links. Clicking on the EKG 1010 may bring up more information relating to the patient's heart condition, or relating to the date of the EKG 1010, for example. Or the user may be able to click on a particular area of the lab results 1011 to bring up more specific information relating to the result, for example. Again, when the user clicks any of the selectable content displayed in FIG. 10B, the user interaction is captured and transmitted from the client device to medical information server 101 for processing, for example, by the ECCD engine hosted by the server. The medical information requested by the user and the additional medical data determined or recommended by the ECCD engine may then be retrieved from the associated data sources 105. The retrieved medical data is then integrated and transmitted from the medical information server 101 to the client device for presentation.

Figure 10C:
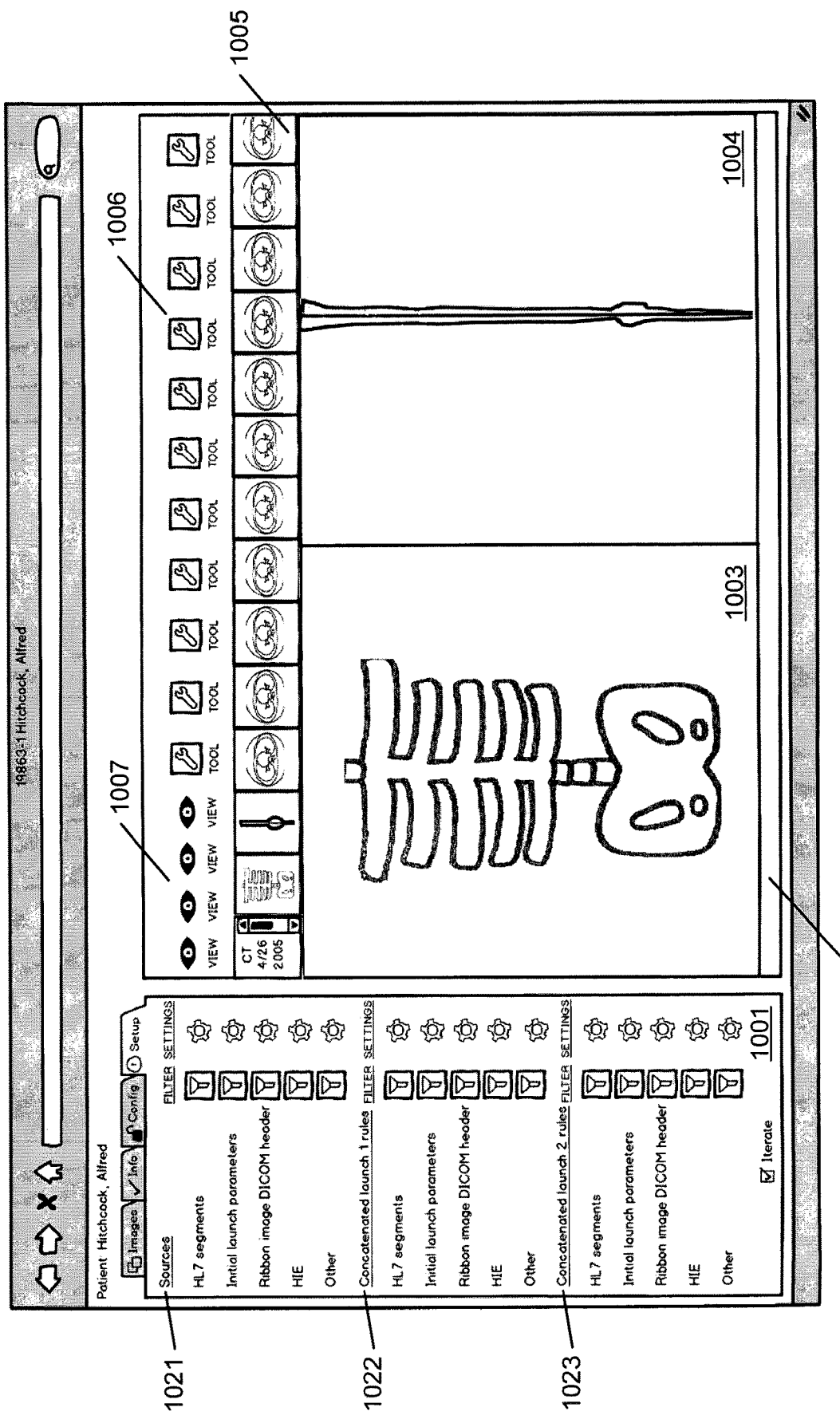

FIG. 10C shows a third possible tab or viewing area within the larger viewer. This tab is labeled "setup" and relates to the rules, filters, and/or settings for the ECCD engine. These rules/filters/settings by the user instruct the ECCD engine on how to query and/or display data in the various viewing areas. In this example, the user can specify via source setting area 1021 which of the data sources from which the ECCD engine should access in order to retrieve medical data. The "concatenated launch 1" 1022 and "concatenated launch 2" 1023 represent settings for different viewing areas or different launches of the viewing areas. Such configuration information can then be transmitted from the client device to the medical information server 101 to be stored therein, such as, for example, as part of user preferences and/or compiled ECCD rules or models. Such settings can be subsequently utilized to determine and retrieve further medical data for the user.

Figure 10D:
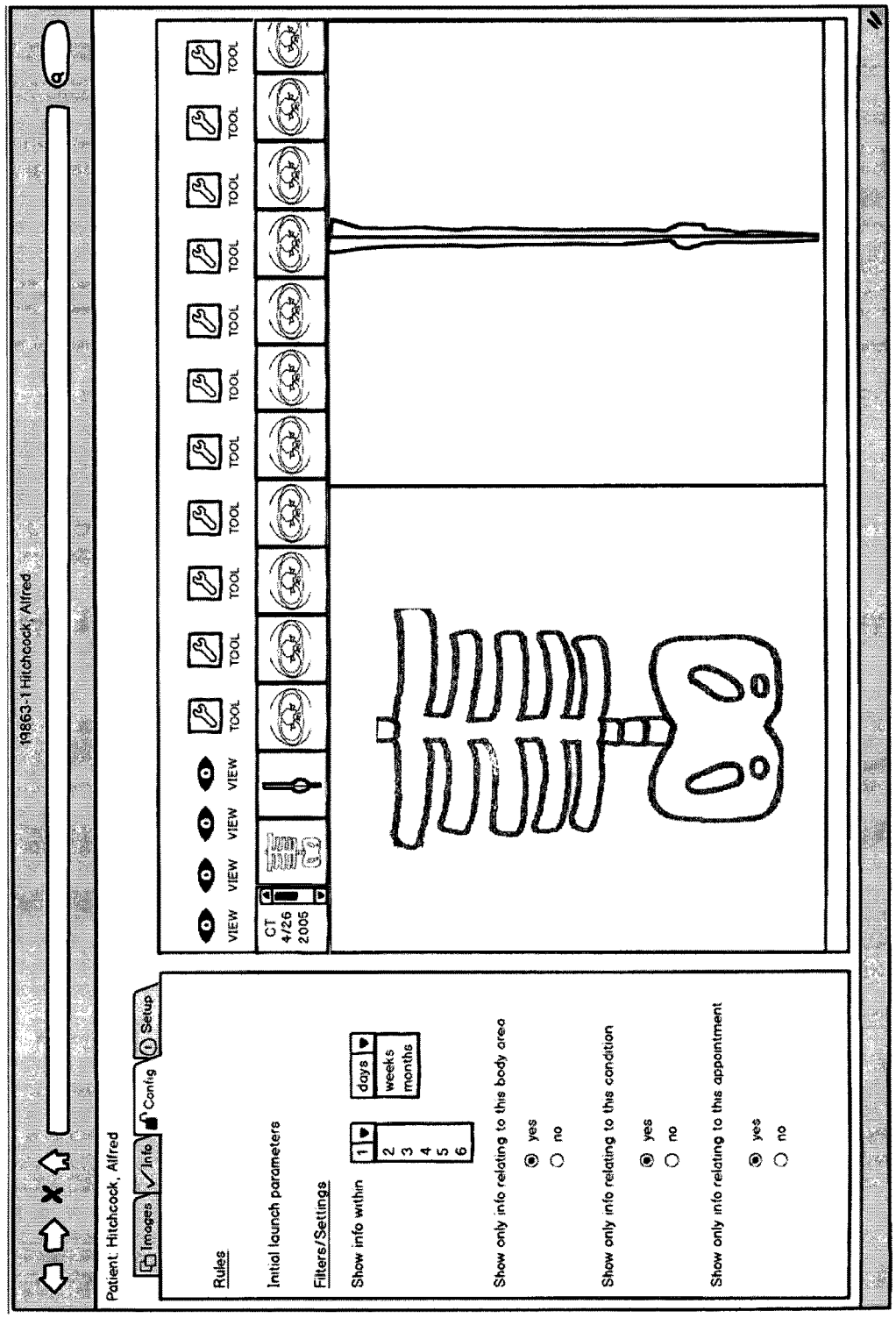

FIG. 10D shows a fourth possible tab or viewing area within the larger viewer. This tab is labeled "config" and is for configuring the viewing areas and queries during the current user session. The configuration can be saved for other viewing sessions as well. In this example, the user is able to configure the parameters of the initial launch of the viewing area(s). The initial launch corresponds to the user clicking a link in the host software package as described earlier. This launches the initial viewing areas and here, in the "config" tab, the user can configure what is shown in the viewing areas upon launch. For example, the user may want to see information relating to a certain time frame and/or a certain body area, condition, appointment/encounter, etc. It should be noted that the user can configure the viewing areas similarly after the initial launch from the hosting software package as well—so these parameters can be configured "on the fly". Direct queries can also be made here, for example, a user can ask to view all data within a certain time frame or relating to a certain data object.

Figure 10E:
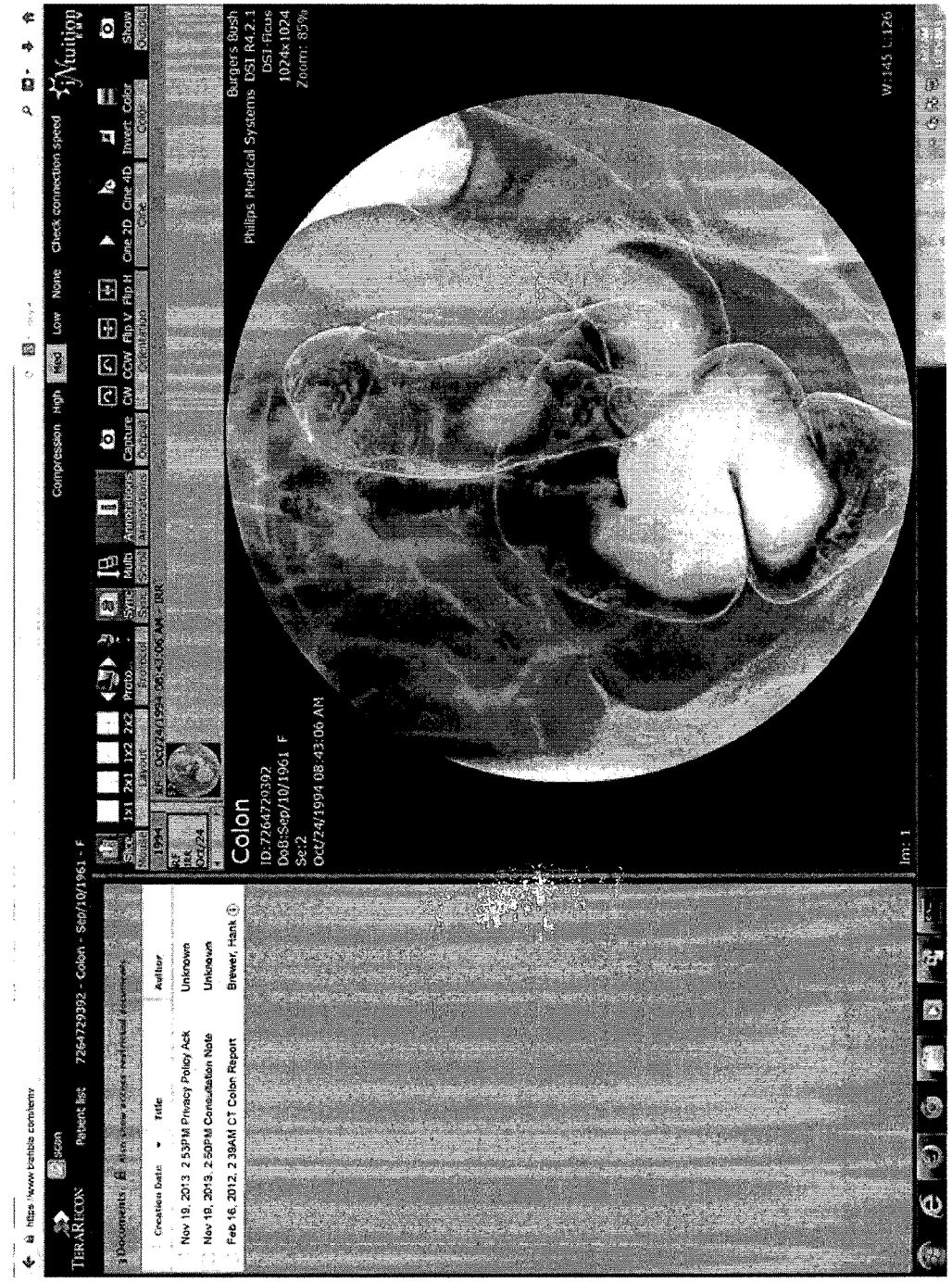

FIG. 10E represents another embodiment of a possible viewer configuration with multiple viewing areas. In this example, the viewer is a web browser and the viewing areas are in frames and/or tabs and/or window areas. The right viewing area shows an image viewing area, where the left viewing area shows a list of additional objects available for this patient, including a privacy policy acknowledgement, a consultation note and a CT colon report, etc. The data in the viewing areas have been provided by the ECCD engine of medical information server 101 as described above. The image viewing area on the right may include several images from one or more image series, DICOM and non-DICOM images, as well as several tools and viewing options. There is also a small scrolling window which shows other CT scan series dates for this patient, as well as one or more display spaces which display enlarged images for closer viewing. The multiple viewer areas are related to each other or "in context". In this example, all the information displayed relates to a particular patient. The information displayed may alternatively relate to a particular patient's event, such as a heart attack, or the information displayed may relate to a particular patient during a particular time frame, or related to a particular appointment or other criteria/criterion.

The tools available may be advanced image processing tools, a list of which is included later in this document. The display of tools may be limited by the ECCD engine to only tools which are relevant to the images being displayed in the viewing area. The user may click on links in any of the viewer areas to alter the information that the ECCD engine displays. For example, the user may click on the CT Colon Report to view a report of a previous colonoscopy side by side with more recent colon images.

Figure 10F:
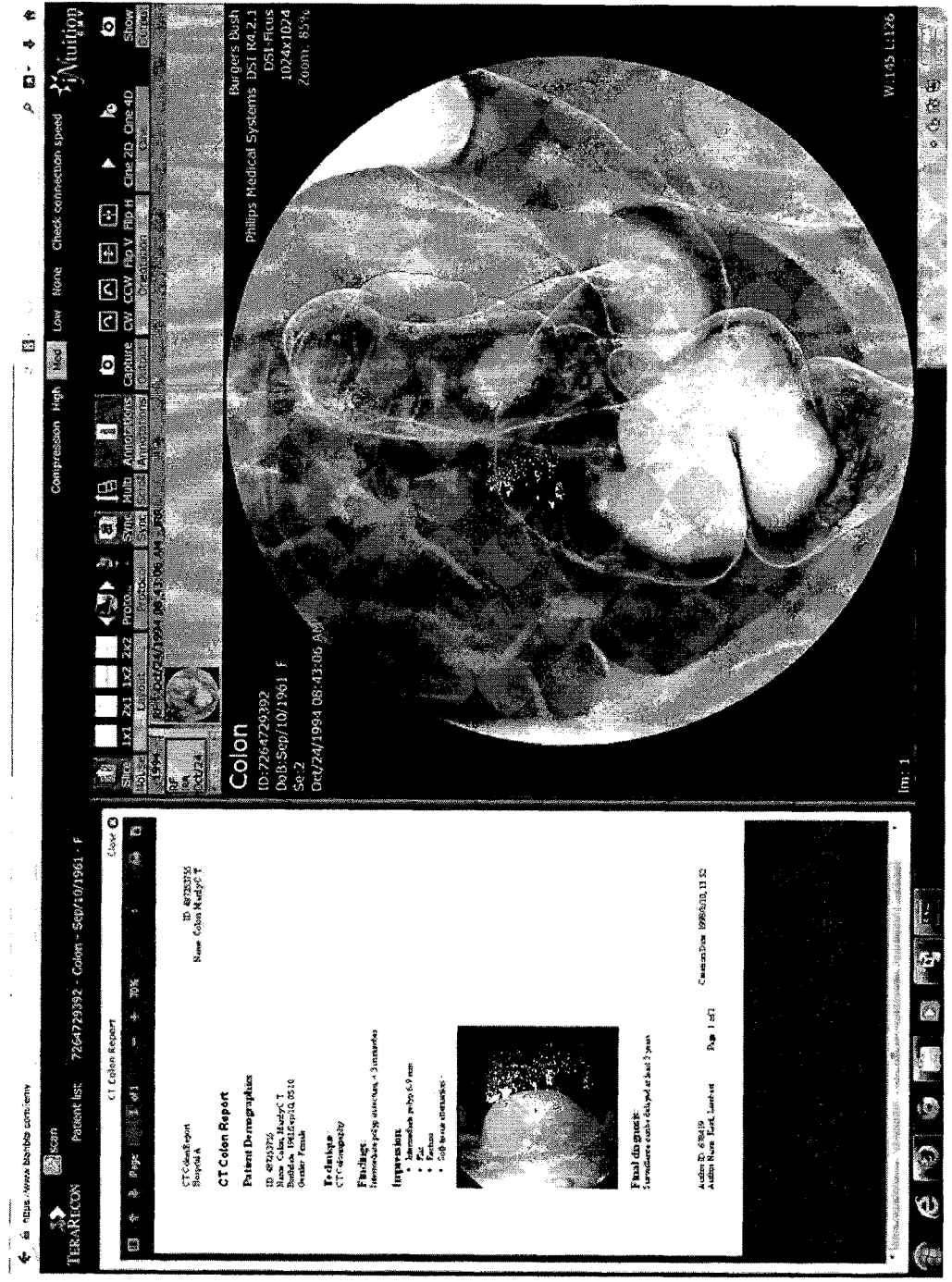

FIG. 10F shows an example of a viewer where the "CT Colon Report" link in the left viewing area has been chosen and a CT colon report is displayed in the left viewing area. Again, this data is displayed "in context" which means they relate to the patient and the images shown in the right viewing area. In this example, the CT colon report shown in the left viewing area relates to the same patient as the colon images in the right viewing area. FIGS. 10 and 11 represent an embodiment of the ECCD engine in which the host software package is an advanced image viewing software package.

Referring back to FIG. 5, in one embodiment, medical imaging processing system 510 includes an image processing engine which provides medical image processing services to clients over a network. The image processing engine may be implemented using dedicated graphics or image processing hardware, such as graphics processing units (GPUs). Medical imaging processing system 510 also includes or is associated with an image store (not shown) to store medical data such as digital imaging and communications in medicine (DICOM) compatible data or other image data, including JPEG, TIFF, video, EKG, laboratory images, reports, text, PDF, sound, and other files. The image store may also incorporate encryption capabilities, where the medical data can be stored and transmitted in an encrypted form. The image store may include multiple databases, and may be implemented with relational database management systems (RDBMS), e.g., Oracle™ database or Microsoft® SQL Server, etc.

In one embodiment, the medical information server 101 includes an access control system (not shown) to control access, by the clients 102, of resources (e.g., image processing tools) and/or medical data stored in image store. Clients 102 may or may not access certain portions or types of resources and/or medical data stored in image store depending upon its access privilege. The access privileges may be determined or configured based on a set of role-based rules or policies. For example, client 102 may be configured with certain roles that only permit access to some of the tools provided by the medical information server 101. In other instances, the client may be configured with certain roles that limit its access to some patient information. For example, certain users (e.g., doctors, medical students) of client 102 may have different access privileges to access different medical information stored in image store 108 or different imaging rendering resources provided by medical information server 101.

Client devices 102 may be a client which may include integrated medical software. In one embodiment, the integrated software integrates image(s) and/or image processing functionality with medical record software (MRS) and/or clinical trial software (CTS), which herein are collectively referred to as medical record and/or clinical software (MRCS). Medical record software (MRS) is patient-centric software that focuses on medical records of the individual patients. Patient-centric means here that the software's primary purpose is to record and view data relating to the individual patient. This type of software may be referred to as electronic medical record (EMR) software, electronic health record (EHR) software, personal health record (PHR) software and other names. Information maintained by the MRS typically includes: patient ID, demographic, info—age, weight, height, Blood Pressure (BP), etc., lab orders and results, test orders and results, medical history, appointment history, appointments scheduled, exam history, prescriptions/medications, symptoms/diagnoses, and insurance/reimbursement info.

Clinical trial software (CTS) includes software for both retrospective and prospective clinical studies. This type of software may be referred to as a clinical trial management system. CTS may also include software for research. CTS is trial-centric which means the primary purpose of the software is to collect and view aggregate data for multiple patients or participants. Although data is collected at the individual patient/participant level, this data is usually viewed "blindly". This means that the viewer and/or analyzer of the data generally do not know the identity of the individual patients/participants. However, data can be viewed at the individual patient/participant level where necessary. This is particularly important where images are involved. CTS typically includes: patient ID, concomitant medications, adverse events, randomization info, data collection, informed consent, aggregated data, and status of study.

In one embodiment, client application 507 running as integrated medical software executed within the client 102A displays medical information of a patient, including, e.g., the medical treatment history of a patient, which may be part of a medical record and/or trial record of the patient. Such records may be downloaded from medical information server 101 in response to a user request and/or recommended by ECCD engine 501. In the case where the integrated medical software integrates MRS, the patient's full identity it typically displayed as part of the medical information. On the other hand, in the case of an integrated CTS, the patient is typically anonymous as discussed above, and the identity of the patient is typically not revealed as part of the displayed medical information.

In one embodiment, image(s) and/or image processing functions may be integrated with the MRCS. Integration can take the form of the image(s) and/or image processing tools showing up in the same window as the MRCS. Integration can also take the form of a window containing the image(s) and/or image processing tools opening up in a separate window from the MRCS window. It should be noted, however, that in either form of integration, the medical information of the patient and image(s) are displayed within the integrated medical software, without requiring the user of the integrated software to separately obtain the images via another software program.

In one embodiment, medical image processing system 510 includes an advanced image processing system and an automatic image processing system (e.g., image processing wizard). When the advanced image processing system is utilized, a set of graphical representation representing a set of image processing tools may be presented in an advanced image processing graphical user interface to allow a user to specify one or more of the image processing tools to process a particular one of images. When the automatic image processing system is utilized, the underlying processing logic of the automatic image processing system is configured to automatically determine and select one or more image processing tools to process the image, for example, without user intervention or user knowledge of which of the image processing tools to be utilized. The graphical representations (e.g., icons) for image processing tools that are provided by the remote imaging processing server 110 are displayed to the user of the integrated medical software executed on the client. In such an embodiment, the available image processing tools are displayed in the integrated medical software as a set of icons or some other graphical representations, which when activated by a user, allow an image to be manipulated by remote imaging processing system 510. In one embodiment the image processing software is integrated with the MRCS program and also opens up "in context." "In context" means that the image processing software opens up to show the appropriate image(s) and/or tools for the current user and/or patient and/or affliction. The availability of imaging tools to a particular user depends on the access privileges of that particular user (e.g., doctors vs. medical students). Alternatively, the availability of imaging tools may be determined based on a particular body part of a patient, which may be identified by certain tags such as DICOM tags.

For example, one doctor may prefer that the cardiovascular images for his patients open up in a 3D view, with vessel centerline tools available, yet the abdominal images for his patients open up in a coronal view with the flythrough, or virtual colonoscopy, tools available. He may prefer to have the other views and tools hidden from view. In another example, another doctor may prefer that the images for her patients open up showing the most recent views and tools that she used for that patient. In another example, the default view for cardiovascular cases may be set to show a particular view and tools, but the user may be able to change the default so that his/her preferences override the default views and tools.

In all of the above examples, ideally only the images that relate to the patient being evaluated at that time are able to be viewed. In addition, the user/physician does not need to search to find the images relating to the patient, the images are automatically associated with the correct patient, for example, based on the corresponding patient ID. To do this, the identity of the patient needs to be associated with the patient's images. This can be done by using tags, such as a common identifier, such as an ID number, metadata associated with one or more of the images, mining patient data, body part analysis, or other ways. Also, the appropriate tools need to be shown and inappropriate tools hidden. The tags are discussed in more details below.

For example, an image or image series can be analyzed to determine whether it is a head, abdomen, or other body part, based on the anatomy. A skull has a characteristic shape, as do other parts of the anatomy. A catalog of reference images may be used to help identify specific body parts. Based on this analysis, the appropriate views and/or tools can be made visible to the user, and inappropriate views and/or tools can be hidden. For example, if the image series is of a head/skull, the image series may be shown in a certain view, such as an axial view, and tools associated with the brain visible. In addition, if certain key words, such as "tumor" or "stroke", are found in the MRCS record, specific tools may be shown, such as tools that detect a tumor or evaluate brain perfusion. It is also possible that a patient ID can be determined from the anatomy in an image based on shape, disease, tags etc. For example, an image of a dental area can be matched with dental records to identify a patient from medical images. Or, an identifying tag can be included in the medical image— such as a tag with the patient ID number placed on or near the table of a CT scanner, or on the patient himself. In another embodiment, the user of the software is able to customize how the image processing software is presented in context. For example, Doctor Y, a cardiologist, may prefer to have the images open up in a 3D model view, and have cardiology tool A and cardiology tool B visible to him. In this example, other views may be hidden (for example, the axial, sagittal, and coronal views) and other tools are hidden (for example, tools relating to the colon or the brain).

According to one embodiment, the advance image processing system allows users of different types to access the imaging tools represented by tool icons for processing images, which utilize processing resources (e.g., image processing engine) over the network. The automatic image processing system allows users of different types to access the functionality of imaging tools without having to deal with the tools directly. The automatic image processing system may be layered on top of, or integrated with, an existing or new advanced medical image processing software system (e.g., advanced image processing system) to simplify or automate the use of the medical image processing resources (e.g., image processing engine), which may be implemented in software, hardware, or a combination of both.

According to one embodiment, both the advanced image processing system and the automatic image process system may access the image processing functions (e.g., libraries, routines, tools, etc.) of the underlying image processing engine via a set of application programming interfaces (APIs) or communication protocols. When the advanced image processing system is utilized, according to one embodiment, an advanced graphical user interface may be presented to allow the user to specify detailed image processing parameters for processing a specific image selected by the user. The underlying processing logic of the advanced image processing system processes the user inputs received from the advanced graphical user interface and formulates one or more image processing commands with a set of image processing parameters that are generated based on the user inputs. The processing logic of the advanced image processing system then sends the commands, for example, via the APIs, to the backend image processing engine to process the image.

When the automatic image processing system is utilized, according to one embodiment, a simplified graphical user interface (e.g., wizard) is presented at a client device of the user to walk the user through a series of simple steps or interactive questions without requiring the user to specify the detailed operational image processing parameters. The underlying processing logic is configured to automatically determine the detailed image processing parameters based on the user interaction with the simplified graphical user interface. A set of image processing commands is generated and sent to the backend image processing engine for processing the image. Alternatively, the underlying processing logic of the automatic image processing system determines the parameters and passes the parameters to the advanced image processing system, just as the advanced image processing system would have received from a user via its corresponding graphical user interface. The advanced image processing system in turn communicates with the underlying image processing engine on behalf of the automatic image processing system.

The automatic image processing system may be implemented in a form of an image processing wizard. The wizard guides a user through the advanced image processing process. The wizard automates as many steps as possible, for example, using preferences, assumptions, and a set of rules, to process image data, such that the user does not have to know the details of how to operate the advanced image processing tools. The wizard also gives the user an opportunity to confirm or change the results that were created automatically or otherwise. The wizard may consist of the presentation of intuitive user interfaces as well as easy to answer questions which help guide the user through the image processing process.

According to one embodiment, the automatic image processing system provides a user friendly interactive graphical user interface. The automatic image processing system allows a user to access the underlying processing resources based on a set of user understandable processing stages to perform certain major or common or popular image processing operations on an image, without having to fully understand specific steps and/or image processing parameters or tools for processing the image. The automatic image processing system, through a user friendly graphical user interface (GUI), may interact with the user through a series of questions and receive user inputs as a part of answers from the user to determine the user's intent. Based on the user interaction with the automatic image processing system, one or more image processing operations may be determined and recommended to the user via the automatic image processing system. The user can select one or more of the recommended image processing operations for processing the image, or alternatively, image processing operations may be performed automatically by the automatic image processing system. Based on a user selection of one or more of the image processing indicators, one or more image processing parameters associated with the selected image processing operations are automatically determined without user intervention and without having the user providing the same parameters.

Based on the image processing parameters received by the automatic image processing system, according to one embodiment, one or more image processing commands are generated and transmitted from the automatic image processing system to the image processing engine for image processing. In response to the image processing commends, the image processing engine processes the image based on the image processing parameters and generates a new or updated image. The new image may represent a different view of the same medical data associated with the original image. The new image is then transmitted from the image processing engine back to the automatic image processing system, which in turn transmits the new image to the client device to be presented to the user. The automatic image processing system also causes the client to prompt the user whether the user is satisfied with the new image. If the user is unsatisfied with the new image, the automatic image processing system may interact with the user for more user inputs concerning the new image and further adjust the image processing parameters and the image processing operations may be iteratively performed. As a result, a user does not have to fully understanding how to utilize the advanced image processing system, although the advanced image processing system may also be available for advanced users. Further detailed information concerning the automatic image processing system can be found in U.S. patent application Ser. No. 14/495,701, filed Sep. 24, 2014, which is incorporated by reference in its entirety.

According to one embodiment, in response to image data received from a medical data center or from image capturing devices (not shown) or from another image source, such as a CD or computer desktop, according to one embodiment, image preprocessing system 510 may be configured to automatically perform certain preprocesses of the image data and store the preprocessed image data in a medical data store (not shown). For example, upon receipt of an image data from PACS or directly from medical image capturing devices, image preprocessing system 204 may automatically perform certain operations, such as bone removal, centerline extraction, sphere finding, registration, parametric map calculation, reformatting, time-density analysis, segmentation of structures, and auto-3D operations, and other operations, some of which are listed later herein.

Image preprocessing system 510 further a workflow management system. The workflow management system may be a separate server or integrated with image processing system 510. The workflow management system performs multiple functions according to some embodiments of the invention. For example, the workflow management system performs a data server function in acquiring and storing medical image data received from the medical image capturing devices. It may also act as a graphic engine or invoke image processing system 510 in processing the medical image data to generate 2D or 3D medical image views. In one embodiment, the workflow management system invokes image processing system 510 having a graphics engine to perform 2D and 3D image generating. When a client requests for certain medical image views, the workflow management system retrieves medical image data stored in medical data store 206, and renders 2D or 3D medical image views from the medical image data. The end results for medical image views are sent to the client.

In one embodiment, the workflow management system manages the creation, update and deletion of workflow templates. It also performs workflow scene creation when receiving user requests to apply a workflow template to medical image data. A workflow is defined to capture the repetitive pattern of activities in the process of generating medical image views for diagnosis. A workflow arranges these activities into a process flow according to the order of performing each activity. Each of the activities in the workflow has a clear definition of its functions, the resource required in performing the activity, and the inputs received and outputs generated by the activity. Each activity in a workflow is referred to as a workflow stage, or a workflow element. With requirements and responsibilities clearly defined, a workflow stage of a workflow is designed to perform one specific task in the process of accomplishing the goal defined in the workflow. For many medical image studies, the patterns of activities to produce medical image views for diagnosis are usually repetitive and clearly defined. Therefore, it is advantageous to utilize workflows to model and document real life medical image processing practices, ensuring the image processing being properly performed under the defined procedural rules of the workflow. The results of the workflow stages can be saved for later review or use.

In one embodiment, a workflow for a specific medical image study is modeled by a workflow template. A workflow template is a template with a predefined set of workflow stages forming a logical workflow. The order of processing an activity is modeled by the order established among the predefined set of workflow stages. In one embodiment, workflow stages in a workflow template are ordered sequentially, with lower order stages being performed before the higher order stages. In another embodiment, dependency relationships are maintained among the workflow stages. Under such arrangement, a workflow stage cannot be performed before the workflow stages it is depending on being performed first. In a further embodiment, advanced workflow management allows one workflow stage depending on multiple workflow stages, or multiple workflow stages depending on one workflow stage, etc.

The image processing operations receive medical image data collected by the medical imaging devices as inputs, process the medical image data, and generate metadata as outputs. Metadata, also known as metadata elements, broadly refers to parameters and/or instructions for describing, processing, and/or managing the medical image data. For instance, metadata generated by the image processing operations of a workflow stage includes image processing parameters that can be applied to medical image data to generate medical image views for diagnostic purpose. Further, various automatic and manual manipulations of the medical image views can also be captured as metadata. Thus, metadata allows the returning of the system to the state it was in when the metadata was saved.

After a user validates the results generated from processing a workflow stage predefined in the workflow template, the workflow management system creates a new scene and stores the new scene to the workflow scene. The workflow management system also allows the updating and saving of scenes during user adjustments of the medical image views generated from the scenes. Further detailed information concerning the workflow management system can be found in co-pending U.S. patent application Ser. No. 12/196,099, entitled "Workflow Template Management for Medical Image Data Processing," filed Aug. 21, 2008, now U.S. Pat. No. 8,370,293, which is incorporated by reference herein in its entirety.

As described above, a variety of image processing tools can be accessed by a user using the image processing system. The following are examples of medical image processing tools that may be included as part of the image processing system described above. These examples are provided for illustrative purposes and not intended to be a limitation of the present invention.

Vessel Analysis tools may include a comprehensive vascular analysis package for CT and MR angiography capable of a broad range of vascular analysis tasks, from coronary arteries to aortic endograft planning and more general vascular review, including carotid and renal arteries. Auto-centerline extraction, straightened view, diameter and length measurements, CPR and axial renderings, and Vessel Track mode for automated thin-slab MIP may be included.

Calcium scoring tools may include Semi-automated identification of coronary calcium with Agatston, volume and mineral mass algorithms. An integrated reporting package with customization options may be included.

Time-dependent analysis tools may include time-resolved planar or volumetric 4D brain perfusion examinations acquired with CT or MR. The TDA tools may support color or mapping of various parameters such as mean enhancement time and enhancement integral, with semi-automated selection of input function and baseline, to speed analysis. TDA tools may support rapid automated processing of dynamic 4D area-detector CT examinations to ensure interpretation within minutes of acquisition.

CT/CTA (Computed tomography angiography) subtraction tools are used in the removal of non-enhancing structures (e.g. bone) from CT angiography examinations, the CT/CTA option includes automatic registration of pre- and post-contrast images, followed by a dense-voxel masking algorithm which removes high-intensity structures (like bone and surgical clips) from the CTA scan without increasing noise, aiding with the isolation of contrast-enhanced vascular structures.

Lobular decomposition tools identify tree-like structures within a volume of interest, e.g. a scan region containing a vascular bed, or an organ such as the liver. The LD tool can then identifies sub-volumes of interest based on proximity to a given branch of the tree or one of its sub-branches. Research applications include the analysis of the lobular structure of organs.

General Enhancement & Noise Treatment with Low Exposure tools may include an advanced volumetric filter architecture applying noise management techniques to improve the effectiveness of 3D, centerline, contouring and segmentation algorithms even when source image quality is not optimum.

The Spherefinder tools perform automated analysis of volumetric examinations to identify the location of structures with a high sphericity index (characteristics exhibited by many nodules and polyps). Spherefinder is often used with Lung or Colon CT scans to identify potential areas of interest.

Segmentation, analysis & tracking tools support analysis and characterization of masses and structures, such as solitary pulmonary nodules or other potential lesions. Tools may identify and segment regions of interest, and then apply measurement criteria, such as RECIST and WHO, leading to tabulated reporting of findings and follow-up comparison. Display and management of candidate markers from optional detection engines may be supported, including Spherefinder.

Time volume analysis tools may provide automated calculation of ejection fraction from a chamber in rhythmic motion, such as a cardiac ventricle. A fast and efficient workflow may be included to enable the user to identify the wall boundaries of interest (e.g. epicardium and endocardium) and, based on these user-confirmed regions of interest, to report ejection fraction, wall volume (mass) and wall thickening from multi-phasic CT data. Tabulated reporting output is included.

Maxillo-facial tools support the analysis and visualization of CT examinations of the Maxillo-facial region, these tools apply the CPR tool to generate "panoramic" projections in various planes and of various thicknesses, and cross-sectional MPR views at set increments along the defined curve plane.

Applicable to endoluminal CT or MR investigations such as colon, lungs, or blood vessels, the Flythrough tools supports side-by-side review, painting of previously-viewed areas, percent coverage tracking, and multiple screen layouts including forward, reverse, fisheye and flat volume rendered views. Tools for contrast subtraction, "Cube View", and integrated contextual reporting may be supported. Display and management of candidate markers from optional detection engines may be supported, including iNtuition's Spherefinder.

The Volumetric Histogram tools allow a volume of interest to be segmented and analyzed for composition. Research applications include the analysis of low-attenuation regions of the lungs, threshold-based division of tumors into voxel populations, investigation of thrombosed vessels or aneurysms, or other pathology.

Findings workflow tools provide a framework for tracking findings across serial examinations. A database holds measurements and key images, and provides support for structured comparisons and tabulated reporting of findings over time, such as the RECIST 1.1 approach for presenting serial comparisons. The Annotation and Image Markup (AIM) XML schema may be supported, for automated integration with voice-recognition systems or clinical databases, and Word-based reports may be derived from the database.

With these tools, any two CT, PET, MR or SPECT series, or any two-series combination thereof can be overlaid with one assigned a semi-transparent color coding and the other shown in grayscale and volume rendering for anatomical reference. Automatic registration is provided and subtraction to a temporary series or to a saved, third series is possible. Support for PET/MR visualization is included.

Certain MR examinations (for example, Breast MR) involve a series of image acquisitions taken over a period of time, where certain structures become enhanced over time relative to other structures. These tools feature the ability to subtract a pre-enhancement image from all post-enhancement images to emphasize visualization of enhancing structures (for example, vascular structures and other enhancing tissue). Time-dependent region-of-interest tools may be provided to plot time-intensity graphs of a given region.

Parametric mapping tools are an enhancement to the Multi-Phase MR tools, the parametric mapping option pre-calculates overlay maps where each pixel in an image is color-coded depending on the time-dependent behavior of the pixel intensity. As an example, this tool can be used in Breast MR to speed identification and investigation of enhancing regions.

The MultiKv tools provide support for Dual Energy and Spectral Imaging acquisitions from multiple vendors, providing standard image processing algorithms such as segmentation or contrast suppression, as well as generic toolkits for precise analysis and development of new techniques.

The embodiments described above can be applied to a variety of medical areas. For example, the techniques described above can be applied to vessel analysis (including Endovascular Aortic Repair (EVAR) and electrophysiology (EP) planning). Such vessel analysis is performed for interpretation of both coronary and general vessel analysis such as carotid and renal arteries, in addition to aortic endograft and electro-physiology planning. Tools provided as cloud services include auto-centerline extraction, straightened view, diameter and length measurements, Curved Planar Reformation (CPR) and axial renderings, as well as charting of the vessel diameter vs. distance and cross-sectional views. The vessel track tool provides a Maximum Intensity Projection (MIP) view in two orthogonal planes that travels along and rotates about the vessel centerline for ease of navigation and deep interrogation. Plaque analysis tools provide detailed delineation of non luminal structure such as soft plaque, calcified plaque and intra-mural lesions.

In addition, the techniques described above can be utilized in the area of endovascular aortic repair. According to some embodiments, vascular analysis tools provided as cloud services support definition of report templates which captures measurements for endograft sizing. Multiple centerlines can be extracted to allow for planning of EVAR procedures with multiple access points. Diameters perpendicular to the vessel may be measured along with distances along the two aorto-iliac paths. Custom workflow templates may be used to enable the major aortic endograft manufactures' measurement specifications to be made as required for stent sizing. Sac segmentation and volume determination with a "clock-face" overlay to aid with documenting the orientation and location of branch vessels for fenestrated and branch device planning, may also be used. Reports containing required measurements and data may be generated.

The techniques described above can also be applied in the left atrium analysis mode, in which semi-automated left atrium segmentation of each pulmonary vein ostium is supported with a single-click distance pair tool, provided as cloud services, for assessment of the major and minor vein diameter. Measurements are automatically detected and captured into the integrated reporting system. These capabilities can be combined with other vessel analysis tools to provide a comprehensive and customized EP planning workflow for ablation and lead approach planning.

The techniques described above can also be utilized in calcium scoring. Semi-automated identification of coronary calcium is supported with Agatston, volume and mineral mass algorithms being totaled and reported on-screen. Results may be stored in an open-format database along with various other data relating to the patient and their cardio-vascular history and risk factors. A customized report can be automatically generated, as part of cloud services, based upon these data. Also includes report generation as defined by the Society of Cardiovascular Computed Tomography (SCCT) guidelines.

The techniques described above can also be utilized in a time-volume analysis (TVA), which may include fully-automated calculation of left ventricular volume, ejection fraction, myocardial volume (mass) and wall thickening from multi-phasic data. A fast and efficient workflow provided as part of cloud services allows for easy verification or adjustment of levels and contours. The results are presented within the integrated reporting function.

The techniques described above can also be utilized in the area of segmentation analysis and tracking (SAT), which includes supports analysis and characterization of masses and structures in various scans, including pulmonary CT examinations. Features include single-click segmentation of masses, manual editing tools to resolve segmentation issues, automatic reporting of dimensions and volume, graphical 3D display of selected regions, integrated automated reporting tool, support for follow-up comparisons including percent volume change and doubling time, and support for review of sphericity filter results.

The techniques described above can also be utilized in the area of flythrough which may include features of automatic segmentation and centerline extraction of the colon, with editing tools available to redefine these centerlines if necessary. 2D review includes side-by-side synchronized supine and prone data sets in either axial, coronal or sagittal views with representative synchronized endoluminal views. 3D review includes axial, coronal and sagittal MPR or MIP image display with large endoluminal view and an unfolded view that displays the entire colon. Coverage tracking is supported to ensure 100% coverage with stepwise review of unviewed sections, one-click polyp identification, bookmark and merge findings, as well as a cube view for isolating a volume of interest and an integrated contextual reporting tool. Support is provided for use of sphericity filter results.

The techniques described above can also be utilized in the area of time-dependent analysis (TDA), which provides assessment tools for analyzing the time-dependent behavior of appropriate computerized tomographic angiography (CTA) and/or MRI examinations, such as within cerebral perfusion studies. Features include support for loading multiple time-dependent series at the same time, and a procedural workflow for selecting input and output function and regions of interest. An integrated reporting tool is provided as well as the ability to export the blood flow, blood volume and transit time maps to DICOM. The tools may also be used with time-dependent MR acquisitions to calculate various time-dependent parameters.

The techniques described above can also be utilized in the area of CTA-CT subtraction, which includes automatic registration of pre- and post-contrast images, followed by subtraction or dense-voxel masking technique which removes high-intensity structures (like bone and surgical clips) from the CTA scan without increasing noise, and leaving contrast-enhanced vascular structures intact.

The techniques described above can also be utilized in dental analysis, which provides a CPR tool which can be applied for review of dental CT scans, offering the ability to generate "panoramic" projections in various planes and of various thicknesses, and cross-sectional MPR views at set increments along the defined curve plane.

The techniques described above can also be utilized in the area of multi-phase MR (basic, e.g. breast, prostate MR). Certain MR examinations (for example, breast, prostate MR) involve a series of image acquisitions taken over a period of time, where certain structures become enhanced over time relative to other structures. This module features the ability to subtract a pre-enhancement image from all post-enhancement images to emphasize visualization of enhancing structures (for example, vascular structures and other enhancing tissue). Time-dependent region-of-interest tools are provided to plot time-intensity graphs of a given region.

The techniques described above can also be utilized in parametric mapping (e.g. for multi-phase Breast MR), in which the parametric mapping module pre-calculates overlay maps where each pixel in an image is color-coded depending on the time-dependent behavior of the pixel intensity. The techniques described above can also be utilized in the area of SphereFinder (e.g. sphericity filter for lung and colon). SphereFinder pre-processes datasets as soon as they are received and applies filters to detect sphere-like structures. This is often used with lung or colon CT scans to identify potential areas of interest. The techniques described can also be utilized in fusion for CT/MR/PET/SPECT. Any two CT, PET, MR or SPECT series, or any two-series combination can be overlaid with one assigned a semi-transparent color coding and the other shown in grayscale and volume rendering for anatomical reference. Automatic registration is provided and subtraction to a temporary series or to a saved, third series is possible.

The techniques described above can also be utilized in the area of Lobular Decomposition. Lobular Decomposition is an analysis and segmentation tool that is designed with anatomical structures in mind. For any structure or organ region which is intertwined with a tree-like structure (such as an arterial and/or venous tree), the Lobular Decomposition tool allows the user to select the volume of interest, as well as the trees related to it, and to partition the volume into lobes or territories which are most proximal to the tree or any specific sub-branch thereof. This generic and flexible tool has potential research applications in analysis of the liver, lung, heart and various other organs and pathological structures.

The techniques described above can also be utilized in the area of Volumetric Histogram. Volumetric Histogram supports analysis of a given volume of interest based on partition of the constituent voxels into populations of different intensity or density ranges. This can be used, for example, to support research into disease processes such as cancer (where it is desirable to analyze the composition of tumors, in an attempt to understand the balance between active tumor, necrotic tissue, and edema), or emphysema (where the population of low-attenuation voxels in a lung CT examination may be a meaningful indicator of early disease).

The techniques described above can also be utilized in the area of Motion Analytics. Motion Analytics provides a powerful 2D representation of a 4D process, for more effective communication of findings when interactive 3D or 4D display is not available. Any dynamic volume acquisition, such as a beating heart, can be subjected to the Motion Analysis, to generate a color-coded "trail" of outlines of key boundaries, throughout the dynamic sequence, allowing a single 2D frame to capture and illustrate the motion, in a manner that can be readily reported in literature. The uniformity of the color pattern, or lack thereof, reflects the extent to which motion is harmonic, providing immediate visual feedback from a single image.

Figure 11A:
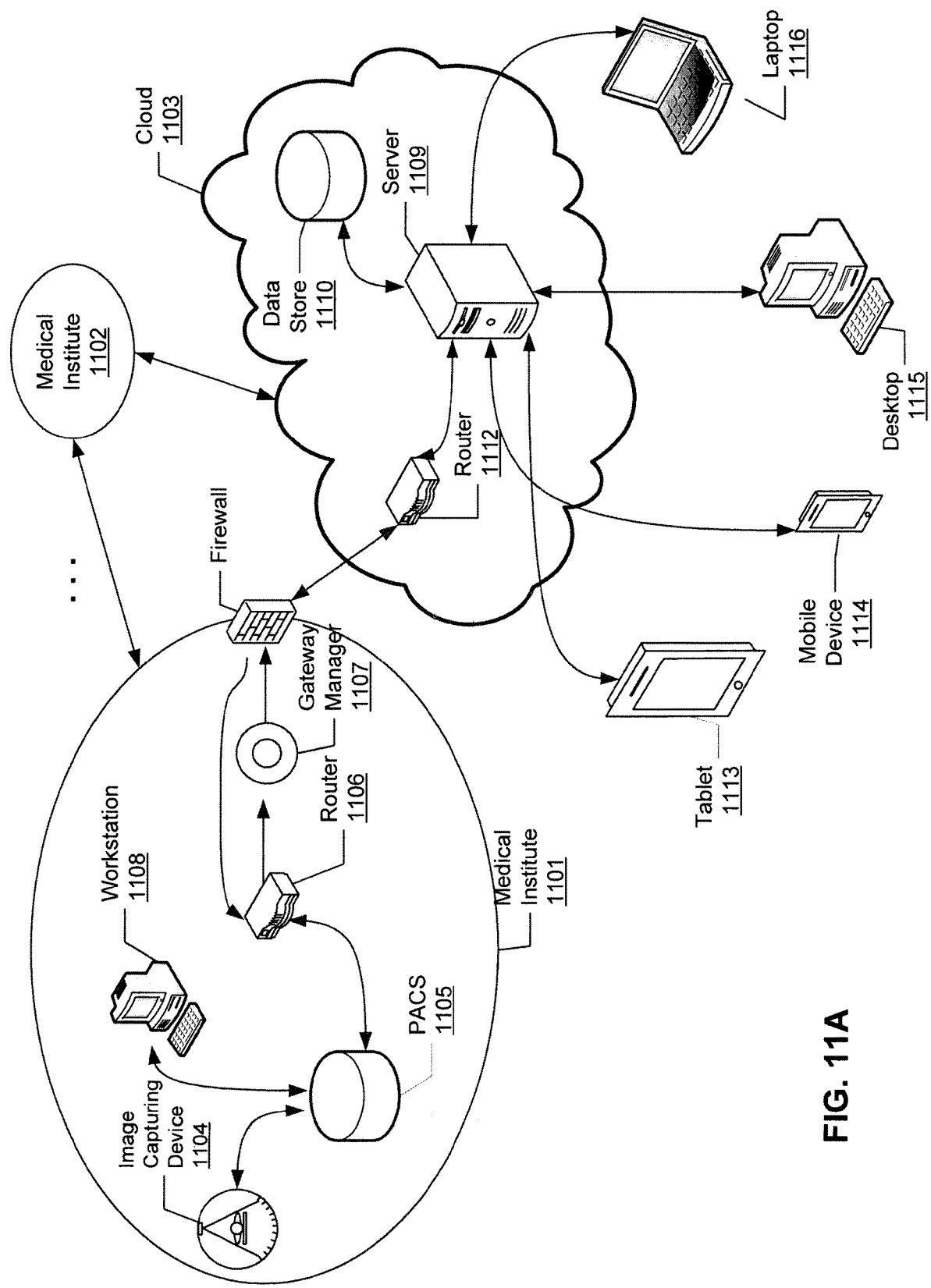
FIGS. 11A and 11B are block diagrams illustrating a cloud-based image processing system according to certain embodiments of the invention.
Figure 11B:
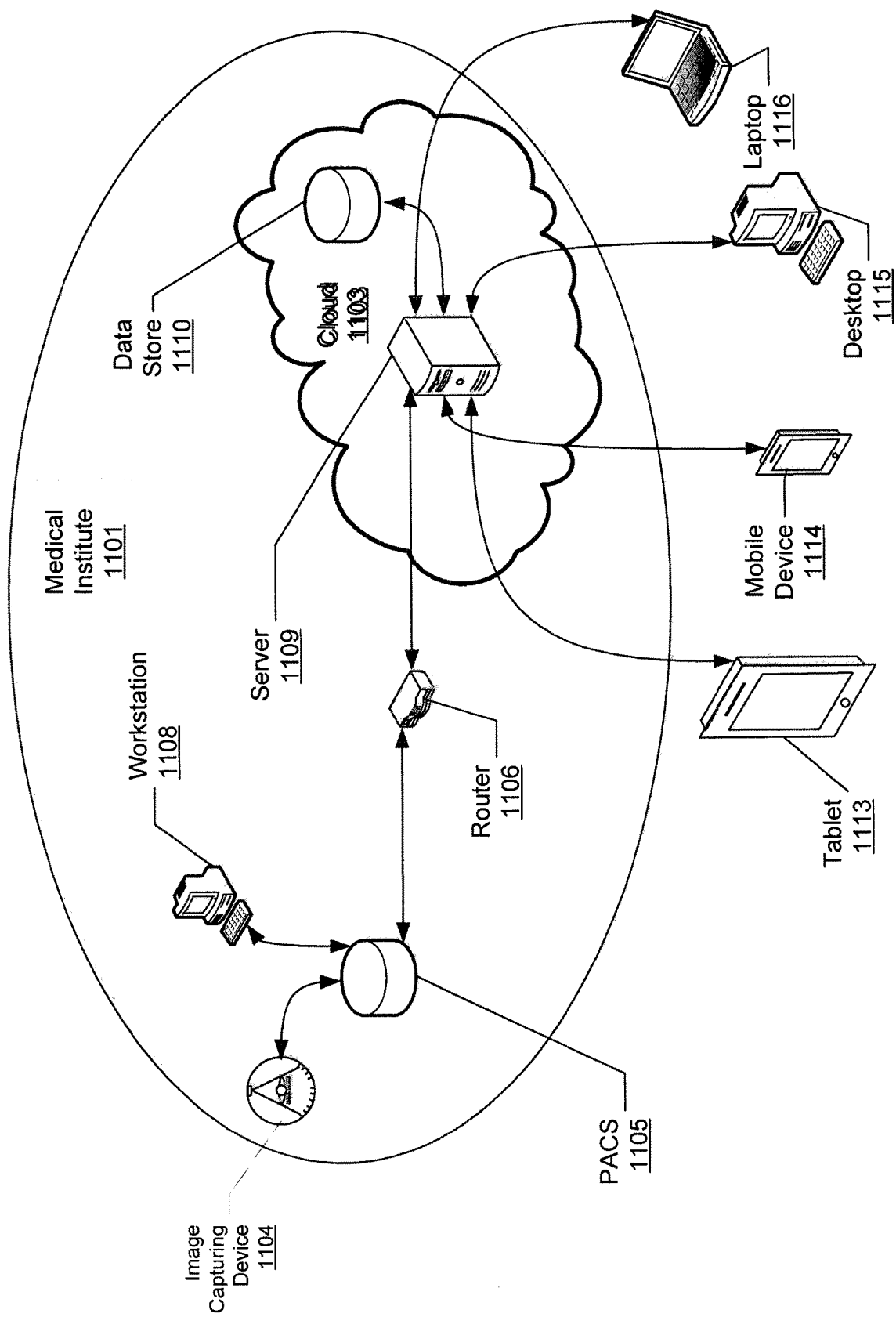

FIGS. 11A and 11B are block diagrams illustrating a cloud-based image processing system according to certain embodiments of the invention. For example, cloud server 1109 may represent medical information server 101 as described above. Referring to FIG. 11A, according to one embodiment, system 1100 includes one or more entities or institutes 1101-1102 communicatively coupled to cloud 1103 over a network. Entities 1101-1102 may represent a variety of organizations such as medical institutes having a variety of facilities residing all over the world. For example, entity 1101 may include or be associated with image capturing device or devices 1104, image storage system (e.g., PACS) 1105, router 1106, and/or data gateway manager 1107. Image storage system 1105 may be maintained by a third party entity that provides archiving services to entity 1101, which may be accessed by workstation 1108 such as an administrator or user associated with entity 1101. Note that throughout this application, a medical institute is utilized as an example of an organization entity. However, it is not so limited; other organizations or entities may also be applied.

In one embodiment, cloud 1103 may represent a set of servers or clusters of servers associated with a service provider and geographically distributed over a network. For example, cloud 1103 may be associated with a medical image processing service provider such as TeraRecon of Foster City, Calif. A network may be a local area network (LAN), a metropolitan area network (MAN), a wide area network (WAN) such as the Internet or an intranet, or a combination thereof. Cloud 1103 can be made of a variety of servers and devices capable of providing application services to a variety of clients such as clients 1113-1116 over a network. In one embodiment, cloud 1103 includes one or more cloud servers 1109 to provide image processing services, one or more databases 1110 to store images and other medical data, and one or more routers 1112 to transfer data to/from other entities such as entities 1101-1102. If the cloud server consists of a server cluster, or more than one server, rules may exist which control the transfer of data between the servers in the cluster. For example, there may be reasons why data on a server in one country should not be placed on a server in another country.

Server 1109 may be an image processing server to provide medical image processing services to clients 1113-1116 over a network. For example, server 1109 may be implemented as part of a TeraRecon AquariusNET™ server and/or a TeraRecon AquariusAPS server. Data gateway manager 1107 and/or router 1106 may be implemented as part of a TeraRecon AquariusGATE device. Medical imaging device 1104 may be an image diagnosis device, such as X-ray CT device, MRI scanning device, nuclear medicine device, ultrasound device, or any other medical imaging device. Medical imaging device 1104 collects information from multiple cross-section views of a specimen, reconstructs them, and produces medical image data for the multiple cross-section views. Medical imaging device 1104 is also referred to as a modality.

Database 1110 may be a data store to store medical data such as digital imaging and communications in medicine (DICOM) compatible data or other image data. Database 1110 may also incorporate encryption capabilities. Database 1110 may include multiple databases and/or may be maintained by a third party vendor such as storage providers. Data store 1110 may be implemented with relational database management systems (RDBMS), e.g., Oracle™ database or Microsoft® SQL Server, etc. Clients 1113-1116 may represent a variety of client devices such as a desktop, laptop, tablet, mobile phone, personal digital assistant (PDA), etc. Some of clients 1113-1116 may include a client application (e.g., thin client application) to access resources such as medical image processing tools or applications hosted by server 1109 over a network. Examples of thin clients include a web browser, a phone application and others.

According to one embodiment, server 1109 is configured to provide advanced image processing services to clients 1113-1116, which may represent physicians from medical institutes, instructors, students, agents from insurance companies, patients, medical researchers, etc. Cloud server 1109, also referred to as an image processing server, has the capability of hosting one or more medical images and data associated with the medical images to allow multiple participants such as clients 1113-1116, to participate in a discussion/processing forum of the images in a collaborated manner or conferencing environment. Different participants may participate in different stages and/or levels of a discussion session or a workflow process of the images.

According to some embodiments, data gateway manager 1107 is configured to automatically or manually transfer medical data to/from data providers (e.g., PACS systems) such as medical institutes. Such data gateway management may be performed based on a set of rules or policies, which may be configured by an administrator or authorized personnel. In one embodiment, in response to updates of medical images data during an image discussion session or image processing operations performed in the cloud, the data gateway manager is configured to transmit over a network (e.g., Internet) the updated image data or the difference between the updated image data and the original image data to a data provider such as PACS 1105 that provided the original medical image data. Similarly, data gateway manager 1107 can be configured to transmit any new images and/or image data from the data provider, where the new images may have been captured by an image capturing device such as image capturing device 1104 associated with entity 1101. In addition, data gateway manager 1107 may further transfer data amongst multiple data providers that is associated with the same entity (e.g., multiple facilities of a medical institute). Furthermore, cloud 1103 may include an advanced preprocessing system (not shown) to automatically perform certain pre-processing operations of the received images using certain advanced image processing resources provided by the cloud systems. In one embodiment, gateway manager 1107 is configured to communicate with cloud 1103 via certain Internet ports such as port 80 or 443, etc. The data being transferred may be encrypted and/or compressed using a variety of encryption and compression methods. The term "Internet port" in this context could also be an intranet port, or a private port such as port 80 or 443 etc. on an intranet.

Figure 12:
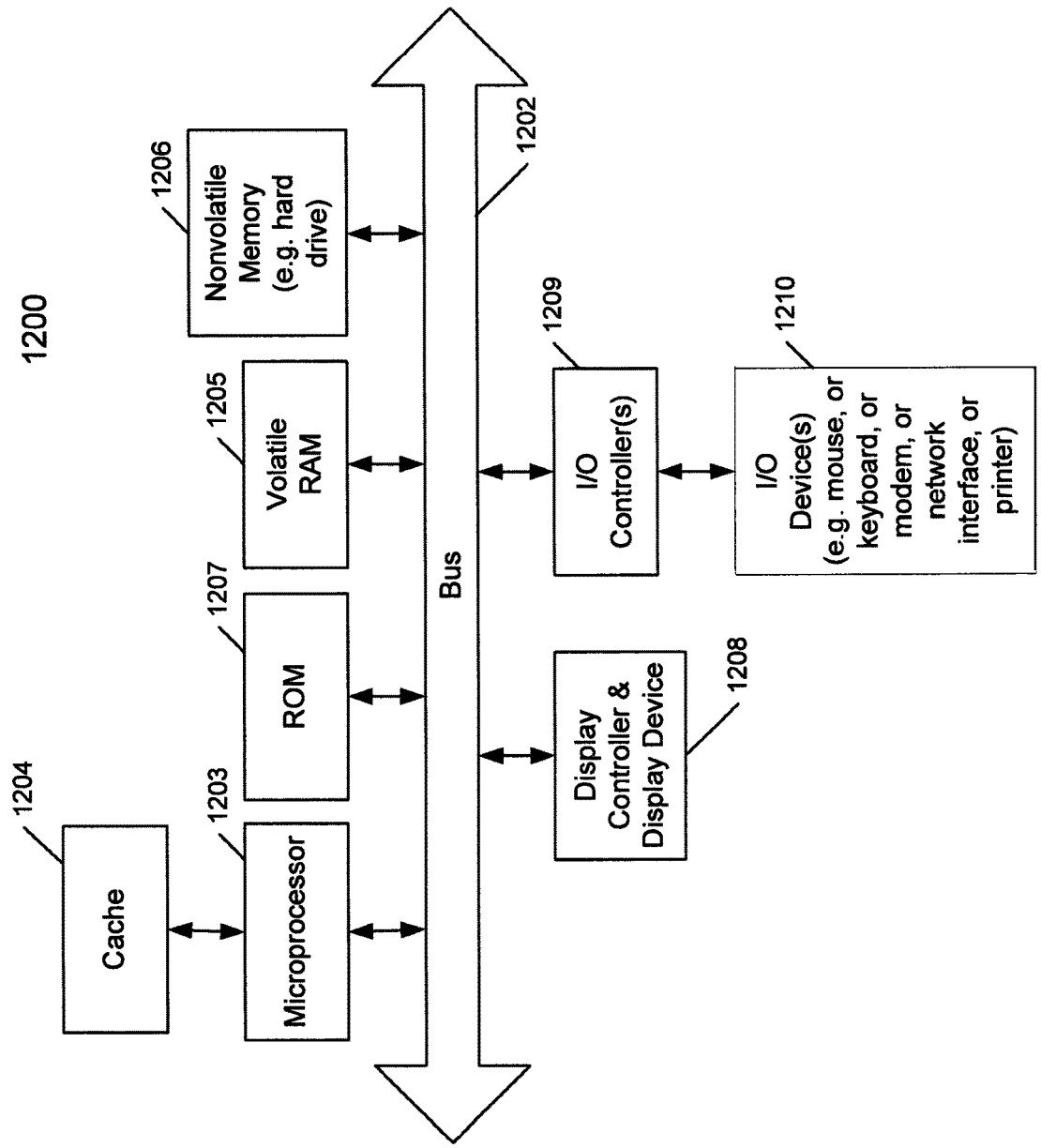
FIG. 12 is a block diagram of a data processing system, which may be used with one embodiment of the invention.

FIG. 12 is a block diagram of a data processing system, which may be used with one embodiment of the invention. For example, the system 1200 may be used as part of a server or a client as described above. For example, system 1200 may represent medical information server 101 described above, which is communicatively coupled to a remote client device or another server via network interface 1210. At least ECCD engine 501, medical image processing system 510, and medical data integrator 505, as described above, may be hosted by system 1200.

Note that while FIG. 12 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used with the present invention.

As shown in FIG. 12, the computer system 1200, which is a form of a data processing system, includes a bus or interconnect 1202 which is coupled to one or more microprocessors 1203 and a ROM 1207, a volatile RAM 1205, and a non-volatile memory 1206. The microprocessor 1203 is coupled to cache memory 1204. The bus 1202 interconnects these various components together and also interconnects these components 1203, 1207, 1205, and 1206 to a display controller and display device 1208, as well as to input/output (I/O) devices 1210, which may be mice, keyboards, modems, network interfaces, printers, and other devices which are well-known in the art.

Typically, the input/output devices 1210 are coupled to the system through input/output controllers 1209. The volatile RAM 1205 is typically implemented as dynamic RAM (DRAM) which requires power continuously in order to refresh or maintain the data in the memory. The non-volatile memory 1206 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 12 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 1202 may include one or more buses connected to each other through various bridges, controllers, and/or adapters, as is well-known in the art. In one embodiment, the I/O controller 1209 includes a USB (Universal Serial Bus) adapter for controlling USB peripherals. Alternatively, I/O controller 1209 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

In the foregoing specification, embodiments of the invention have been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method for imaging a specimen and providing resulting medical image data to a client device that includes a display, the method comprising:

storing medical data in a plurality of medical data sources, wherein medical data sources in the plurality of medical data sources have different interfaces, so that more than one interface is required to be used to access all the medical data sources in the plurality of medical data sources, including:
using a medical imaging device to capture multiple cross section views of the specimen and to reconstruct the captured multiple cross section views to produce medical image data that is included as part of the medical data;

receiving interaction information resulting from first user interaction on the client device performed by a user, the first user interaction resulting from review of information pertaining to a first patient, a user action analysis module analyzing the interaction to produce results;

invoking a first set of evolving contextual clinical data (ECCD) rules associated with the user based on the first user interaction to determine one or more medical data categories that are likely to be of interest to the user, wherein the first set of ECCD rules are generated by a user behavioral analyzer within an ECCD engine that derives user behavioral patterns based on prior user interactions with different medical information presented to the user with respect to reviewing different medical information of patients;

using the results and the ECCD rules for the user to predict what additional medical data should be provided to first user that pertains to the first patient;

using one of a plurality of interface modules to obtain the additional medical data from the plurality of medical data sources, each module from the plurality of interface modules being used to retrieve medical data from one medical data source in the plurality of medical data sources, including:
retrieving medical report data from a laboratory information server; and providing the additional medical data to the client device to be displayed on the display.

2. The method of claim 1, further comprising, prior to receiving the interaction information resulting from first user interaction on the client device:

monitoring and capturing the prior user interactions with different medical information presented to the user;

performing, by the ECCD engine, an analysis using an algorithm on the captured prior user interactions to derive the user behavioral patterns in response to the different medical information; and generating, by the ECCD engine, the first set of ECCD rules based on the user behavioral patterns.

3. The method of claim 2, further comprising:
receiving a second user interaction of the user with respect to one or more views of medical information displayed at the client device;
training an ECCD model in view of the second user interaction to generate a second set of one or more ECCD rules, which is an update from the first set of ECCD rules; and
storing the second set of ECCD rules in a user database associated with the user, wherein the second set of ECCD rules are used, in lieu of the first set of ECCD rules, to predict future medical information likely of interest to the user.

4. The method of claim 1, further comprising, for each of the medical data sources, maintaining a medical data interface to specifically communicate with a corresponding medical data source using a compatible communication protocol.

5. The method of claim 4, wherein the medical data sources are operated by different organizations.

6. The method of claim 1, wherein medical data categories comprise medical images, electronic medical records, laboratory information, and hospital information.

7. The method of claim 6, wherein the medical data sources comprise a picture archiving and information system (PACS), an electronic medical record (EMR) server, a laboratory information server, and a hospital information system.

8. The method of claim 1, wherein the additional medical data comprises second medical data that is not requested by the user, but is recommended by the first set of ECCD rules.

9. The method of claim 1, further comprising:
determining based on the first set of ECCD rules a set of one or more image processing tools that the user likely uses; and
transmitting tool information representing a set of image processing tools to the client device, wherein the set of image processing tools is presented as a set of graphical representations at the client device.

10. The method of claim 1, wherein the medical data of the medical data categories is retrieved from more than one medical data servers.

11. The method of claim 1, wherein the medical data categories are determined further based on a second set of ECCD rules that is associated with metadata of medical information displayed at the client device.

12. A system that images a specimen and integrates resulting medical image data with other medical data, the system comprising:
a client device that includes a display;
a plurality of medical data sources, each medical data source in the plurality of medical data sources storing medical data, wherein medical data sources in the plurality of medical data sources have different interfaces, so that more than one interface is required to be used to access all the medical data sources in the plurality of medical data sources;
a medical imaging device that captures multiple cross section views of a specimen and reconstructs the multiple cross section views to produce the medical image data that is included as part of the medical data;
a user interaction analyzer, carried out on a processor, to receive a signal from a client device over a network, the signal representing a first user interaction of a user with respect to first medical information displayed at the client device, to invoke a first set of one or more evolving contextual clinical data (ECCD) rules associated with the user based on the first user interaction to determine one or more medical data categories that are likely to be of interest to the user;
an ECCD engine, carried out on the processor, that derives behavioral patterns of the user based on prior user interactions with different medical information presented to the user, the ECCD engine including:
a user behavioral analyzer that analyzes user interactive data of each user in a plurality of users to determine user behavioral patterns with respect to reviewing different medical information of patients, and
a rule engine that generates a first set of ECCD rules for each user in the plurality of users;
a data retrieval module carried out on the processor, coupled to the user interaction analyzer to access the plurality of medical data sources to retrieve the medical data; and
a view generator, carried out on the processor, coupled to the data retrieval module to integrate retrieved medical image data to generate one or more views of medical information and to transmit the one or more views of the medical information to the client device to be displayed on the display of the client device.

13. The system of claim 12, further comprising:
a user data collector to monitor and capture the prior user interactions with different medical information presented to the user; and
an ECCD engine to perform an analysis using an algorithm on the captured prior user interactions to derive the behavioral patterns of the user in response to the different medical information and to generate the first set of ECCD rules based on the behavioral patterns of the user.

14. The system of claim 13, wherein the user interaction analyzer is to receive a second user interaction of the user with respect to one or more views of second medical information displayed at the client device, and wherein the ECCD engine is to train an ECCD model in view of the second user interaction to generate a second set of ECCD rules, which is an update from the first set of ECCD rules and to store the second set of ECCD rules in a user database associated with the user, wherein the second set of ECCD rules are used, in lieu of the first set of ECCD rules, to predict future medical information likely of interest to the user.

15. The system of claim 12, wherein the ECCD engine learns from the user by requesting feedback from the user.

16. The system of claim 12, wherein the ECCD engine and a data integrator are located within a medical information server.

17. The system of claim 12, wherein the prior user interactions are captured and stored as an interaction history that is used by the ECCD engine to train or adjust the ECCD rules for the user.

18. The system of claim 12, additionally comprising:
a user data collector that monitors click through rates and view times by the user that are used by the ECCD engine to train or adjust the ECCD rules for the user.

19. The system of claim 12, wherein the ECCD engine learns from the user by tracking total interpretation that the user uses to review information or perform advanced image processing steps.

20. A system that images a specimen and integrates resulting medical image data with other medical data, the system comprising:
- a client device that includes a display;
- a plurality of medical data sources, each medical data source in the plurality of medical data sources storing medical data, wherein medical data sources in the plurality of medical data sources have different interfaces, so that more than one interface is required to be used to access all the medical data sources in the plurality of medical data sources;
- a medical imaging device that captures multiple cross section views of a specimen and reconstructs the multiple cross section views to produce the medical image data that is included as part of the medical data; and
- a medical information server, including:
  - an evolving contextual clinical data (ECCD) engine that includes:
    - a user behavioral analyzer that analyzes user interactive data of each user in a plurality of users to determine user behavioral patterns with respect to reviewing different medical information of patients, and
    - a rule engine that generates a set of ECCD rules for each user in the plurality of users, and
  - a plurality of interface modules, each module from the plurality of modules being used to retrieve medical data from one medical data source in the plurality of medical data sources;
- wherein the medical information server receives interaction information resulting from user interactions on the client device performed by a first user in the plurality of users, the user interactions resulting from review of information pertaining to a first patient, and produces from the interaction information results that are forwarded to the ECCD engine;
- wherein the ECCD engine uses the ECCD rules for the first user to predict what additional medical data should be provided to the first user that pertains to the first patient; and
- wherein the medical information server uses at least one of the plurality of interface modules to obtain the additional medical data from the plurality of medical data sources, and then provides the additional medical data to the client device.

21. The system of claim 20, wherein the medical information server includes a data integrator that interfaces with the plurality of interface modules.

22. The system of claim 20, wherein the interaction information or the results are captured and stored as an interaction history that is used by the ECCD engine to train or adjust the ECCD rules for the first user.

23. The system of claim 20, wherein the medical information server additionally includes:
- a user data collector that monitors click through rates and view times by the first user that are used by the ECCD engine to train or adjust the ECCD rules for the first user.

24. The system of claim 20, wherein the ECCD engine learns from the first user by tracking total interpretation that the first user uses to review information or perform advanced image processing steps.

25. The system of claim 20, wherein the ECCD engine learns from the first user by requesting feedback from the user.

26. The method of claim 1, wherein the ECCD engine is located within a medical information server.

27. The method of claim 1, wherein the interaction information or the results are captured and stored as an interaction history that is used by the ECCD engine to train or adjust the ECCD rules for the user.

28. The method of claim 1, additionally comprising:
- monitoring click through rates and view times by the user that are used by the ECCD engine to train or adjust the ECCD rules for the user.

29. The method of claim 1, additionally comprising:
- wherein the ECCD engine learns from the user by tracking total interpretation that the user uses to review information or perform advanced image processing steps.

30. The method of claim 1, wherein the ECCD engine learns from the user by requesting feedback from the user.

* * * * *